(12) United States Patent
Montgomery et al.

(10) Patent No.: US 10,736,578 B2
(45) Date of Patent: Aug. 11, 2020

(54) SYSTEMS AND METHODS OF MONITORING AUTOREGULATION

(71) Applicant: COVIDIEN LP, Mansfield, MA (US)

(72) Inventors: Dean Montgomery, Edinburgh (GB); Paul S. Addison, Edinburgh (GB); Peter Galen, Portland, OR (US)

(73) Assignee: COVIDIEN LP, Mansfield, MA (US)

( * ) Notice: Subject to any disclaimer, the term of this patent is extended or adjusted under 35 U.S.C. 154(b) by 511 days.

(21) Appl. No.: 15/648,665

(22) Filed: Jul. 13, 2017

(65) Prior Publication Data

US 2018/0014791 A1 Jan. 18, 2018

Related U.S. Application Data

(60) Provisional application No. 62/362,325, filed on Jul. 14, 2016, provisional application No. 62/362,329, filed on Jul. 14, 2016.

(51) Int. Cl.
*A61B 5/00* (2006.01)
*A61B 5/1455* (2006.01)
(Continued)

(52) U.S. Cl.
CPC ............ *A61B 5/7275* (2013.01); *A61B 5/021* (2013.01); *A61B 5/14551* (2013.01);
(Continued)

(58) Field of Classification Search
CPC ... A61B 5/7275; A61B 5/14551; A61B 5/021; A61B 5/14553; A61B 5/4064; A61B 5/7246; G16H 50/30
See application file for complete search history.

(56) References Cited

U.S. PATENT DOCUMENTS 4,776,339 A  10/1988  Schreiber
5,351,685 A  10/1994  Potratz
(Continued)

FOREIGN PATENT DOCUMENTS

EP        615723 A1     9/1994
WO     WO9843071 A1    10/1998
(Continued)

OTHER PUBLICATIONS

Chuan et al., "Is cerebrovascular autoregulation associated with outcomes after major noncardiac surgery? A prospective observational pilot study," Acta Anaesthesiol Scand., Aug. 5, 2018, 10 pp.
(Continued)

*Primary Examiner* — Eric F Winakur
*Assistant Examiner* — Abid A Mustansir
(74) *Attorney, Agent, or Firm* — Shumaker & Sieffert, P.A.

(57) ABSTRACT

A system for monitoring autoregulation includes an oxygen saturation sensor configured to obtain an oxygen saturation signal indicative of an oxygen saturation of a patient. The system also includes a controller having a processor configured to receive a blood pressure signal indicative of a blood pressure of the patient and the oxygen saturation signal, determine a change in the oxygen saturation signal and a change in the blood pressure signal over a period of time, and provide an indication that the patient's autoregulation is intact if the oxygen saturation changes by more than an oxygen saturation threshold and if the blood pressure changes by less than a blood pressure threshold during the period of time.

20 Claims, 10 Drawing Sheets

(51) Int. Cl.
*A61B 5/021* (2006.01)
*G16H 50/30* (2018.01)
(52) U.S. Cl.
CPC ........ *A61B 5/14553* (2013.01); *A61B 5/4064* (2013.01); *A61B 5/7246* (2013.01); *G16H 50/30* (2018.01)

(56) References Cited

U.S. PATENT DOCUMENTS

| | | | |
|---|---|---|---|
| 5,482,034 | A | 1/1996 | Lewis et al. |
| 5,533,507 | A | 7/1996 | Potratz |
| 5,577,500 | A | 11/1996 | Potratz |
| 5,584,296 | A | 12/1996 | Cui et al. |
| 5,626,140 | A | 5/1997 | Feldman et al. |
| 5,803,910 | A | 9/1998 | Potratz |
| 5,934,277 | A | 8/1999 | Mortz |
| 6,385,471 | B1 | 5/2002 | Mortz |
| 6,438,399 | B1 | 8/2002 | Kurth |
| 6,453,183 | B1 | 9/2002 | Walker |
| 6,505,060 | B1 | 1/2003 | Norris |
| 6,510,329 | B2 | 1/2003 | Heckel |
| 6,599,251 | B2 | 7/2003 | Chen et al. |
| 6,668,182 | B2 | 12/2003 | Hubelbank |
| 6,714,803 | B1 | 3/2004 | Mortz |
| 6,754,516 | B2 | 6/2004 | Mannheimer |
| 6,896,661 | B2 | 5/2005 | Dekker |
| 6,987,994 | B1 | 1/2006 | Mortz |
| 7,001,337 | B2 | 2/2006 | Dekker |
| 7,221,969 | B2 | 5/2007 | Stoddart et al. |
| 7,268,873 | B2 | 9/2007 | Sevick-Muraca et al. |
| 7,744,541 | B2 | 6/2010 | Baruch et al. |
| 8,556,811 | B2 | 10/2013 | Brady |
| 2004/0097797 | A1 | 5/2004 | Porges et al. |
| 2005/0004479 | A1 | 1/2005 | Townsend et al. |
| 2005/0033129 | A1 | 2/2005 | Edgar, Jr. et al. |
| 2005/0192488 | A1 | 9/2005 | Bryenton et al. |
| 2005/0192493 | A1 | 9/2005 | Wuori |
| 2007/0004977 | A1 | 1/2007 | Norris |
| 2007/0049812 | A1 | 3/2007 | Aoyagi et al. |
| 2008/0081974 | A1 | 4/2008 | Pav |
| 2008/0146901 | A1 | 6/2008 | Katura et al. |
| 2008/0200785 | A1 | 8/2008 | Fortin |
| 2008/0228053 | A1 | 9/2008 | Wang et al. |
| 2009/0326386 | A1 | 12/2009 | Sethi et al. |
| 2010/0010322 | A1* | 1/2010 | Brady ............... A61B 5/02028 600/301 |
| 2010/0030054 | A1 | 2/2010 | Baruch et al. |
| 2010/0049082 | A1 | 2/2010 | Hu et al. |
| 2011/0046459 | A1 | 2/2011 | Zhang et al. |
| 2011/0105912 | A1 | 5/2011 | Widman et al. |
| 2012/0130697 | A1* | 5/2012 | Woodford ............ A61B 5/0205 703/11 |
| 2012/0149994 | A1 | 6/2012 | Luczyk et al. |
| 2012/0253211 | A1 | 10/2012 | Brady et al. |
| 2012/0271130 | A1 | 10/2012 | Benni |
| 2013/0190632 | A1 | 7/2013 | Baruch et al. |
| 2014/0073888 | A1 | 3/2014 | Sethi et al. |
| 2014/0073930 | A1* | 3/2014 | Sethi .................. A61B 5/02007 600/473 |
| 2014/0275818 | A1 | 9/2014 | Kassem et al. |
| 2014/0278285 | A1 | 9/2014 | Marmarelis et al. |
| 2016/0106372 | A1 | 4/2016 | Addison et al. |
| 2016/0324425 | A1 | 11/2016 | Addison et al. |
| 2016/0345913 | A1 | 12/2016 | Montgomery et al. |
| 2016/0367197 | A1 | 12/2016 | Addison et al. |
| 2017/0000395 | A1 | 1/2017 | Addison et al. |
| 2017/0000423 | A1 | 1/2017 | Addison et al. |
| 2017/0095161 | A1 | 4/2017 | Addison et al. |
| 2017/0105631 | A1 | 4/2017 | Addison et al. |
| 2017/0105672 | A1 | 4/2017 | Addison et al. |

FOREIGN PATENT DOCUMENTS

| | | |
|---|---|---|
| WO | WO0059374 | 10/2000 |
| WO | WO03000125 A1 | 1/2003 |
| WO | WO03071928 A2 | 9/2003 |
| WO | WO2004075746 A2 | 9/2004 |
| WO | WO2008097411 A1 | 8/2008 |
| WO | WO2016182853 A1 | 11/2016 |

OTHER PUBLICATIONS

Addison, P. S., et al.; "Low-Oscillation Complex Wavelets," Journal of Sound and Vibration, 2002, vol. 254, Elsevier Science Ltd., pp. 1-30.

Addison, P. S.; "The Illustrated Wavelet Transform Handbook," 2002, IOP Publishing Ltd., Bristol, UK, Ch. 2.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Barreto, Armando B., et al.; "Adaptive LMS Delay Measurement in dual Blood Volume Pulse Signals for Non-Invasive Monitoring," *IEEE*, pp. 117-120 (1997).

Bassan, Haim, et al.; "Identification of pressure passive cerebral perfusion and its mediators after infant cardiac surgery," Pediatric Research Foundation, vol. 57, No. 1, 2005; pp. 35-41.

Belal, Suliman Yousef, et al.; "A fuzzy system for detecting distorted plethysmogram pulses in neonates and paediatric patients," *Physiol. Meas.*, vol. 22, pp. 397-412 (2001).

Brady, Ken M., et al.; "Continuous Measurement of Autoregulation by Spontaneous Fluctuations in Cerebral Perfusion Pressure Comparison of 3 Methods," NIH Public Access Author Manuscript, Stroke, 2008, 39(9), pp. 1-13.

Brady, Ken M., et al.; "Continuous time-domain analysis of cerebrovascular autoregulation using near-infrared spectroscopy," American Stroke Association, DOI:10.1161/strokeaha.107.485706, Aug. 2007, pp. 2818-2825.

Brady, Ken M., et al.; "Monitoring cerebral blood flow pressure autoregulation in pediatric patients during cardiac surgery," Stroke 2010;41:1957-1962 (http://stroke.ahajournals.org/content/41/9/1957.full).

Brady, Ken M., et al.; "Noninvasive Autoregulation Monitoring with and without Intracranial Pressure in a Naive Piglet Brain," Neuroscience in Anesthesiology and Perioperative Medicine, 2010, vol. 111, No. 1, International Anesthesia Research Society, pp. 191-195.

Brady, Kenneth, et al.; "Real-Time Continuous Monitoring of Cerebral Blood Flow Autoregulation Using Near-Infrared Spectroscopy in Patients Undergoing Cardiopulmonary Bypass," Stroke, 2010, 41, American Heart Association, Inc., pp. 1951-1956.

Caicedo, Alexander, et al.; "Cerebral Tissue Oxygenation and Regional Oxygen Saturation Can be Used to study Cerebral Autoregulation in Prematurely Born Infants," Pediatric Research, vol. 69, No. 6, Jun. 1, 2011, pp. 548-553.

Caicedo, Alexander, et al.; "Detection of cerebral autoregulation by near-infrared spectroscopy in neonates: performance analysis of measurement methods," Journal of Biomedical Optics 17 (11) pp. 117003-1-117003-9 (Nov. 2012).

Chan, K.W., et al.; "17.3: Adaptive Reduction of Motion Artifact from Photoplethysmographic Recordings using a Variable Step-Size LMS Filter," IEEE, pp. 1343-1346 (2002)+A10.

Chen, Li, et al.; "The role of pulse oximetry plethysmographic waveform monitoring as a marker of restoration of spontaneous circulation: a pilot study," Chin Crit Care Med, 2015, vol. 27, No. 3, pp. 203-208.

Chen, Liangyou, et al.; "IS respiration-induced variation in the photoplethysmogram associated with major hypovolemia in patients with actue tramatic injuries," Shock, vol. 34, No. 5, pp. 455-460 (2010).

Cheng, Ran, et al.; "Noninvasive optical evaluation of spontaneous low frequency oscillations in cerebral hemodynamics", Neuroimage, Academic Press, vol. 62, No. 3, May 24, 2012, pp. 1445-1454.

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

(56) References Cited

OTHER PUBLICATIONS

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.
Cysewska-Sobusaik, Anna; "Metrological Problems With noninvasive Transillumination of Living Tissues," *Proceedings of SPIE*, vol. 4515, pp. 15-24 (2001).
Czosnyka, Marek, et al.; "Monitoring of cerebrovascular autoregulation: Facts, Myths, and Missing Links," Neurocrit Care (2009) 10:373-386.
Daubechies, Ingrid, et al.; "A Nonlinear Squeezing of the Continuous Wavelet Transform Based on Auditory Nerve Models," Princeton University, 1996, Acoustic Processing Department, NY, pp. iii, 1-17.
Daubechies, Ingrid, et al.; "Synchrosqueezed Wavelet Transforms: an Empirical Mode Decomposition-like Tool," Princeton University, 2010, Applied and Computational Harmonic Analysis, pp. 1-32.
Dias, Celeste, et al.; "Optimal Cerebral Perfusion Pressure Management at Bedside: A Single-Center Pilot Study," Neurocritical care, vol. 23, No. 1, Jan. 8, 2015; pp. 92-102; ISSN: 1541-6933.
East, Christine E., et al.; "Fetal Oxygen Saturation and Uterine Contractions During Labor," *American Journal of Perinatology*, vol. 15, No. 6, pp. 345-349 (Jun. 1998).
Edrich, Thomas, et al.; "Can the Blood Content of the Tissues be Determined Optically During Pulse Oximetry Without Knowledge of the Oxygen Saturation?—an in-Vitro Investigation," *Proceedings of the 20th Annual International conference of the IEEE Engie in Medicine and Biology Society*, vol. 20, No. 6, p. 3072-3075, 1998.
Eichhorn, Lars, et al.; "Evaluation of newar-infrared spectroscopy under apnea-dependent hypoxia in humans," Journal of Clinical Monitoring and Computing, vol. 29, No. 6, Feb. 4, 2015, pp. 749-757.
Gao, Yuanjuin, et al.; "Response of cerebral tissue oxygenation and arterial blood pressure to postural change assessed by wavelet phase coherence analysis", 2014 7th International conference on Biomedical Engineering and Informatics, IEEE, Oct. 14, 2014, pp. 373-377.
Ge, Z.; "Significance tests for the wavelet cross spectrum and wavelet linear coherence," Annales Geophysicae, 2008, 26, Copernicus Publications on behalf of European Geosciences Union, pp. 3819-3829.
Gesquiere, Michael J., et al., "Impact of withdrawal of 450 ML of blook on respiration-induced oscillations of the ear plethysmographic waveform," Journal of Clinical Monitoring and Computing (2007) 21:277-282.
Goldman, Julian M.; "Masimo Signal Extraction Pulse Oximetry," *Journal of Clinical Monitoring and Computing*, vol. 16, pp. 475-483 (2000).
Gommer, Erik D., et al.; "Dynamic cerebral autoregulation: different signal processing methods without influence on results and reproducibility"; Medical & Biological Engineering & Computer; vol. 48, No. 12, Nov. 4, 2010; pp. 1243-1250.
Hamilton, Patrick S., et al.; "Effect of Adaptive Motion-Artifact Reduction on QRS Detection," *Biomedical Instrumentation & Technology*, pp. 197-202 (May-Jun. 2000).
Huang, J., et al.; "Low Power Motion Tolerant Pulse Oximetry," Anesthesia & Analgesia 2002 94: S103.
Johansson, A.; "Neural network for photoplethysmographic respiratory rate monitoring," *Medical & Biological Engineering & Computing*, vol. 41, pp. 242-248 (2003).
Kaestle, S.; "Determining Artefact Sensitivity of New Pulse Oximeters in Laboratory Using Signals Obtained from Patient," *Biomedizinische Technik*, vol. 45 (2000).
Kim, J.M., et al.; "Signal Processing Using Fourier & Wavelet Transform for pulse oximetry," pp. II-310-II-311 (2001).
Kirkham, S.K., et al.; "A new mathematical model of dynamic cerebral autoregulation based on a flow dependent feedback mechanism; Dynamic cerebral autoregulation modelling," Physiological Measurement, Institute of Physics Publishing, vol. 22, No. 3, Aug. 1, 2001; (13 pgs.).
Leahy, Martin J., et al.; "Sensor Validation in Biomedical Applications," *IFAC Modelling and Control in Biomedical Systems*, Warwick, UK; pp. 221-226 (1997).
Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.
Lee, Jennifer K., et al.; A pilot study of cerebrovascular reactivity autoregulation after pediatric cardiac arrest, Resuscitation 85, 2014, Elsevier Ireland Ltd., pp. 1387-1393.
Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).
Massart, Desire L., et al.; "Least Median of Squares: A Robust Method for Outlier and Model Error Detection in Regression and Calibration," Analytica Chimica Acta, 1986, Elsevier Science Publishers B.V., The Netherlands, pp. 171-179.
McGrath, S.P., et al.; "Pulse oximeter plethysmographic waveform changes in awake, spontaneously breathing, hypovolemic volunteers," Anesth. Analg. vol. 112 No. 2, pp. 368-374 (2010).
Montgomery, Dean, et al.; "Data cluestering methods for the determination of cerebral autoregulation functionality," Journal of Clinical Monitoring and Computing, vol. 30, No. 5, Sep. 16, 2015, pp. 661-668.
Morren, G., et al.; "Detection of autoregulation in the brain of premature infants using a novel subspace-based technique," 23rd Annual International Conference of IEEE Engineering in Medicine and Biology Society, Oct. 2001; pp. 1-4.
Morren, Geert, et al.; "Quantitation of the concordance between cerebral intravascular oxygenation and mean arterial blood pressure for the detection of impaired autoregulation," 29th Annual Meeting of the International Society on Oxygen Transport to Tissue, UofP, Aug. 2001; pp. 1-5.
Neumann, R., et al.; "Fourier Artifact suppression Technology Provides Reliable $SpO_2$," Anesthesia & Analgesia 2002, 94: S105.
Obrig, Hellmuth, et al.; "Spontaneous low frequency oscillations of cerebral heodynamics and metabolism in human adults," NeuroImage 12, 623-639 (2000).
Odagiri, Y.; "Pulse Wave Measuring Device," *Micromechatronics*, vol. 42, No. 3, pp. 6-11 (published Sep. 1998) (Article in Japanese—contains English summary of article).
Ono, Masahiro, et al.; "Validation of a stand-alone near-infrared spectroscopy system for monitoring cerebral autoregulaiton during cardiac surgery," International Anethesia Research Society, Jan. 2013, vol. 116, No. 1, pp. 198-204.
Panerai, B.; "Cerebral Autoregulation: from models to clinical Applications," Cardiovascular Engineering: an International Journal, vol. 8, No. 1, Nov. 28, 2007, (28 pgs.).
Payne, Stephen J., et al.; "Tissue Oxygenation Index as a Measure of Cerebral Autoregulation," Biomedial Engineering, Feb. 2004, Innsbruck, Austria, pp. 546-550.
Reinhard, Matthias, et al.; "Spatial mapping of dynamic cerebral autoregulation by multichannel near-infrared spectrosccopy in high-grade carotid artery disease", International Society for optical Engineering, SPIE, vol. 19, No. 9, Sep. 1, 2014, p. 97005.
Reinhard, Matthias, et al.; "Oscillatory cerebral hemodynamics—the macro- vs. microvascular level," Journal of the Neurological Sciences 250 (2006) 103-109.
Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.
Rowley, A.B., et al.; "Synchronization between arterial blood pressure and cerebral oxyhaemoglobin concentration investigated by wavelet cross-correlation," Physiol. Meas., vol. 28, No. 2, Feb. 2007, pp. 161-173.
Shamir, M., et al.; "Pulse oximetry plethysmographic waveform during changes in blood volume," British Journal of Anaesthesia 82(2): 178-81 (1999).

(56) References Cited

OTHER PUBLICATIONS

Sorensen, Henrik, et al.; "A note on arterial to venous oxygen saturation as reference for NIRS-determined frontal lobe oxygen saturation in healthy humans," Frontiers in Physiology, vol. 4, Art. 403, Jan. 2014, pp. 1-3.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Tsuji, Miles, et al.; "Cerebral intravascular oxygenation correlates with mean arterial pressure in critically ill premature infants," American Academy of Pediatrics, 2000; 106; pp. 625-632.

Wagner, Bendicht P., et al.; "Dynanic cerebral autoregulatory response to blood pressure rise measured by near-infrared spectroscopy and intracranial pressure," Critical Care Medicine 2002, vol. 30, No. 9, pp. 2014-2021.

Whitaker, E., et al.; "Cerebrovascular Autoregulation After Pediatric Cardiac Arrest," Neuro-85, 2012, 2 pgs.

Williams, Monica, et al.; "Intraoperative blood pressure and Cerebral perfusion: strategies to clarify hemodynamic goals," Paediatric Anaesthesia, vol. 24, No. 7, Jul. 12, 2014; pp. 657-667; XP055331904.

Wong, Flora Y., et al.; "Impaired Autoregulation in preterm infants identified by using spatially resolved spectroscopy," American Academy of Pediatrics DOI:10.1542 (2008) e604-611.

Wu Dongmei, et al.; "Na*/H* Exchange inhibition delays the onset of hypovolemic circulatory shock in pigs," Shock, vol. 29, No. 4, pp. 519-525 (2008).

Wu, et al.; "Using synchrosqueezing transform to discover breathing dynamics from ECG signals," arXiv:1105.1571, vol. 2, Dec. 2013, pp. 1-9.

Wu, Hau-tieng, et al.; "Evaluating physiological dynamics via Synchrosqueezing: Prediction of Ventilator Weaning," Journal of Latex Class Files, vol. 11, No. 4, Dec. 2012, pp. 1-9.

Zhang, Rong, et al.; "Transfer function analysis of dynamic cerebral autoregulation in humans," 1998 the American Physiological Society; pp. H233-H241.

Zweifel, Christian, et al.; "Continuous time-domain monitoring of cerebral autoregulation in neurocritical care," Medical Engineering & Physics, Elsevier Ltd., vol. 36, No. 5, 2014, pp. 638-645.

U.S. Appl. No. 15/666,167, filed Aug. 1, 2017, naming inventors Addison et al.

\* cited by examiner

| BLOOD PRESSURE / OXYGEN SATURATION | INCREASE ↑ | DECREASE ↓ | STABLE → | |
|---|---|---|---|---|
| INCREASE ↑ | IMPAIRED | INTACT | INTACT | ~62 |
| DECREASE ↓ | INTACT | IMPAIRED | INTACT | ~64 |
| STABLE → | UNDETERMINED | UNDETERMINED | UNDETERMINED | ~66 |

| BLOOD PRESSURE \ OXYGEN SATURATION | INCREASE ↑ | DECREASE ↓ | STABLE → |
|---|---|---|---|
| INCREASE ↑ | IMPAIRED | INTACT | INTACT |
| DECREASE ↓ | INTACT | IMPAIRED | INTACT |
| STABLE → | INTACT | INTACT | UNDETERMINED |

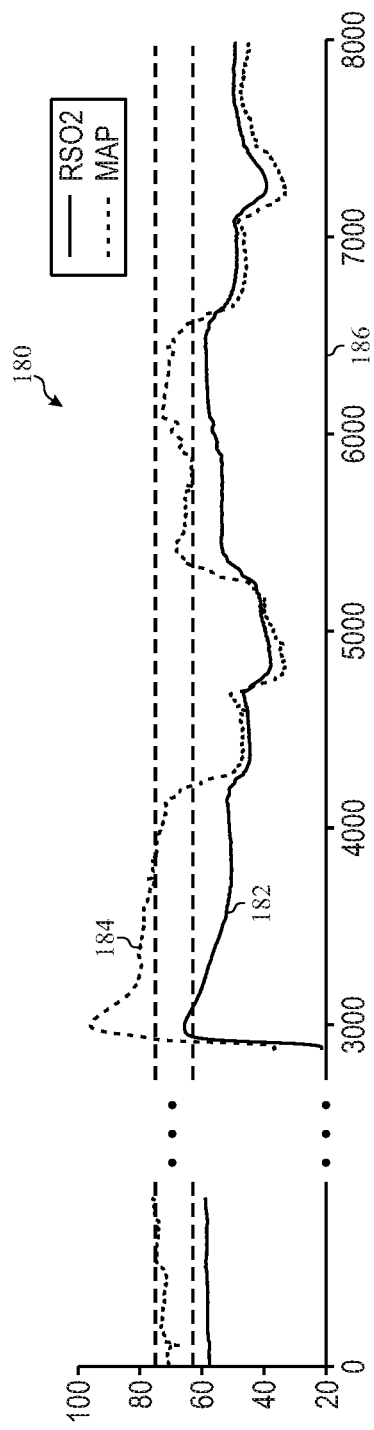
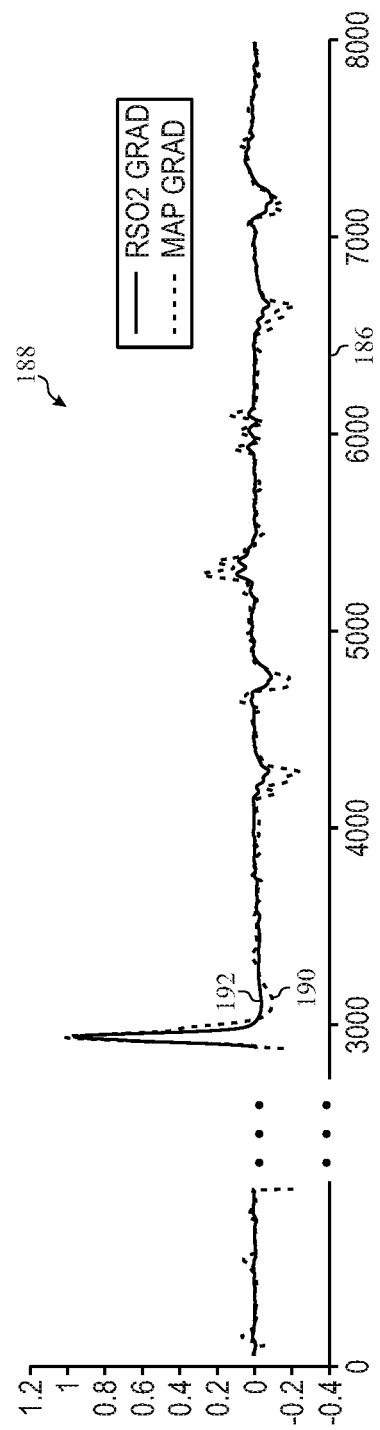
FIG. 9A
FIG. 9B

SYSTEMS AND METHODS OF MONITORING AUTOREGULATION

CROSS-REFERENCE TO RELATED APPLICATIONS

This application claims priority to and the benefit of Provisional Application No. 62/362,325, entitled "SYSTEMS AND METHODS OF MONITORING AUTOREGULATION USING GRADIENT MATCHING," filed Jul. 14, 2016, and Provisional Application No. 62/362,329, entitled "SYSTEM AND METHOD OF MONITORING AUTOREGULATION," filed Jul. 14, 2016, which are herein incorporated by reference in their entirety for all purposes.

BACKGROUND

The present disclosure relates generally to medical devices and, more particularly, to systems and methods of monitoring autoregulation.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical professionals often desire to monitor certain physiological parameters of their patients. In some cases, clinicians may wish to monitor a patient's autoregulation. Autoregulation is a physiological process that attempts to maintain an optimal cerebral blood flow to supply appropriate levels of oxygen and nutrients to the brain. During autoregulation, cerebral arterioles dilate or constrict to maintain optimal blood flow. For example, as cerebral pressure decreases, cerebral arterioles dilate in an attempt to maintain blood flow. As cerebral pressure increases, cerebral arterioles constrict to reduce the blood flow that could cause injury to the brain. If the patient's autoregulation process is not functioning properly, the patient may experience inappropriate cerebral blood flow, which may have negative effects on the patient's health. In particular, a drop in cerebral blood flow may cause ischemia, which may result in tissue damage or death of brain cells. An increase in cerebral blood flow may cause hyperemia, which may result in swelling of the brain or edema.

Some existing systems for monitoring autoregulation may determine a patient's autoregulation status based on a correlation coefficient. However, such a correlation coefficients may be subject to various sources of error. Furthermore, many data points may be required to reliably calculate such correlation coefficients. Accordingly, an extended period of time (e.g., several minutes, or even hours) may pass before such systems are able to provide a reliable indication of the patient's autoregulation status. In certain clinical settings, the extended time for determining whether the patient's autoregulation is intact or impaired may affect patient care and outcomes. Therefore, systems and methods for efficiently and reliably determining the patient's autoregulation status are provided herein.

BRIEF DESCRIPTION OF THE DRAWINGS

Advantages of the disclosed techniques may become apparent upon reading the following detailed description and upon reference to the drawings in which:

FIG. 9A is an example of a graph illustrating an oxygen saturation signal and a blood pressure signal over a period of time;

FIG. 9B is an example of a graph illustrating a gradient of oxygen saturation and a gradient of blood pressure over the period of time based on the signals of FIG. 9A;

DETAILED DESCRIPTION OF SPECIFIC EMBODIMENTS

Figure 1:
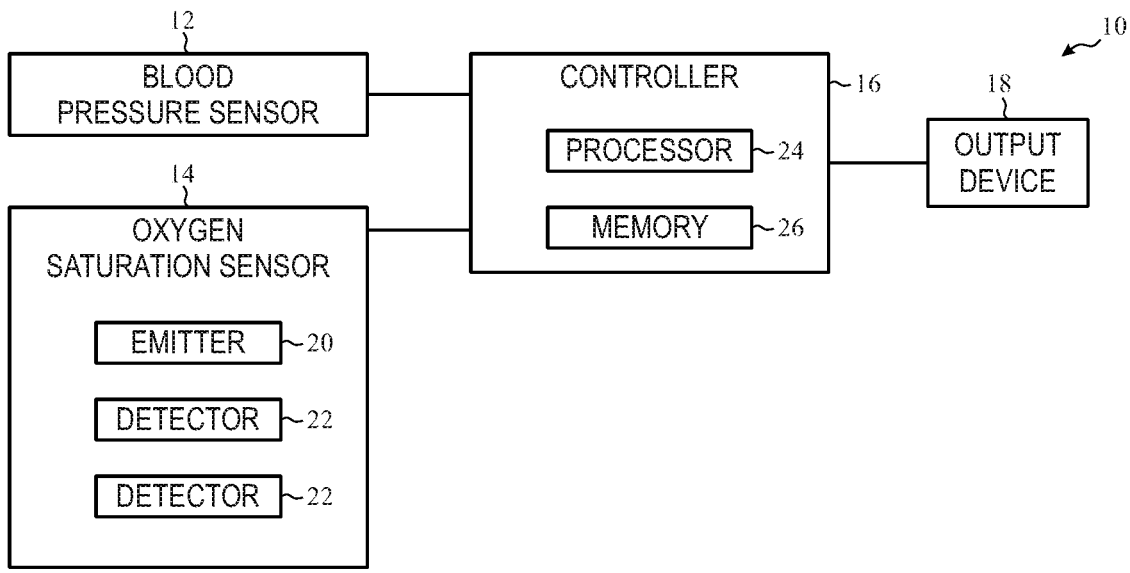
FIG. 1 is a block diagram of an embodiment of a system for monitoring a patient's autoregulation.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A physician may monitor a patient's autoregulation through the use of various monitoring devices and systems. In some cases, a system may include a controller (e.g., an electronic controller having a processor and a memory) that is configured to monitor a patient's autoregulation by based on measurements of the patient's blood pressure (e.g., mean arterial blood pressure) and measurements of the patient's oxygen saturation (e.g., regional oxygen saturation). In some cases, a cerebral oximetry index (COx) may be derived based at least in part on a linear correlation between the patient's blood pressure and oxygen saturation. However, as discussed in more detail below, the COx may not accurately reflect the patient's autoregulation status during periods of time when the patient's blood pressure is generally stable.

In view of the foregoing, during autoregulation monitoring, it may be desirable to determine whether the patient's blood pressure varies by more than a threshold (e.g., a blood pressure threshold, such as approximately 1, 2, 3, 4, or 5 millimeters of mercury [mmHg]) over a period of time (e.g., approximately 0.5, 1, 2, 3, 4, 5, or more minutes). In certain embodiments, the controller may calculate the COx only if the patient's blood pressure varies by more than the threshold over the period of time. In certain embodiments, the controller may discard the COx and/or may not provide (e.g., display) the COx if the patient's blood pressure varies by less than the threshold over the period of time. For example, a change in the patient's blood pressure that exceeds the threshold over the period of time may cause the controller to calculate and/or to provide an indication of the COx, while a change in the patient's blood pressure that is less than the threshold over the period of time may block the controller from calculating and/or displaying the indication of the COx. In certain embodiments, the controller may display a prior COx (e.g., a most recent COx value, a most recent COx value at the same blood pressure, or an average or a weighted average of previously calculated COx values at the same blood pressure) if the patient's blood pressure varies by less than the threshold.

In certain embodiments, the controller may determine whether the patient's blood oxygen saturation varies by more than a threshold (e.g., an oxygen saturation threshold, such as approximately 1, 2, 3, 4, or 5 percent) over the period of time. In some such cases, the controller may determine and/or provide an indication (e.g., via a display or a speaker) that the patient's autoregulation is intact if the blood pressure varies by less than the blood pressure threshold and if the oxygen saturation varies by more than the oxygen saturation threshold over the period of time. For example, a change in the patient's blood pressure that is less than the blood pressure threshold over the period of time in combination with a change in the patient's oxygen saturation that exceeds the oxygen saturation threshold over the period of time may cause the controller to determine and/or to provide an indication that the patient's autoregulation is intact. Thus, the disclosed systems and methods may provide improved patient monitoring and patient care.

FIG. 1 illustrates an embodiment of a system 10 configured to monitor autoregulation. As shown, the system 10 includes a blood pressure sensor 12, an oxygen saturation sensor 14 (e.g., a regional oxygen saturation sensor), a controller 16 (e.g., an electronic controller), and an output device 18. The blood pressure sensor 12 may be any sensor or device configured to obtain the patient's blood pressure (e.g., mean arterial blood pressure). For example, the blood pressure sensor 12 may include a blood pressure cuff for non-invasively monitoring blood pressure or an arterial line for invasively monitoring blood pressure. In certain embodiments, the blood pressure sensor 12 may include one or more pulse oximetry sensors. In some such cases, the patient's blood pressure may be derived by processing time delays between two or more characteristic points within a single plethysmography (PPG) signal obtained from a single pulse oximetry sensor. Various techniques for deriving blood pressure based on a comparison of time delays between certain components of a single PPG signal obtained from a single pulse oximetry sensor is described in U.S. Publication No. 2009/0326386, entitled "Systems and Methods for Non-Invasive Blood Pressure Monitoring," the entirety of which is incorporated herein by reference. In other cases, the patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus," the entirety of which is incorporated herein by reference, multiple PPG signals may be obtained from the multiple pulse oximetry sensors, and the PPG signals may be compared against one another to estimate the patient's blood pressure. Regardless of its form, the blood pressure sensor 12 may be configured to generate a blood pressure signal indicative of the patient's blood pressure (e.g., arterial blood pressure) over time. As discussed in more detail below, the blood pressure sensor 12 may provide the blood pressure signal to the controller 16 or to any other suitable processing device to enable evaluation of the patient's autoregulation status.

As shown, the oxygen saturation sensor 14 may be a regional oxygen saturation sensor configured to generate an oxygen saturation signal indicative of blood oxygen saturation within the venous, arterial, and capillary systems within a region of the patient. For example, the oxygen saturation sensor 14 may be configured to be placed on the patient's forehead and may be used to calculate the oxygen saturation of the patient's blood within the venous, arterial, and capillary systems of a region underlying the patient's forehead (e.g., in the cerebral cortex). In such cases, the oxygen saturation sensor 14 may include an emitter 20 and multiple detectors 22. The emitter 20 may include at least two light emitting diodes (LEDs), each configured to emit at different wavelengths of light, e.g., red or near infrared light. In some embodiments, light drive circuitry (e.g., within a monitor or within the sensor 14) may provide a light drive signal to drive the emitter 20 and to cause the emitter 20 to emit light. In one embodiment, the LEDs of the emitter 20 emit light in the range of about 600 nm to about 1000 nm. In a particular embodiment, one LED of the emitter 20 is configured to emit light at about 730 nm and the other LED of the emitter 20 is configured to emit light at about 810 nm. One of the detectors 22 is positioned relatively "close" (e.g., proximal) to the emitter 20 and one of the detectors 22 is positioned relatively "far" (e.g., distal) from the emitter 22. Light intensity of multiple wavelengths may be received at both the "close" and the "far" detectors 22. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation ($rSO_2$) signal for the target tissues over time. As discussed in more detail below, the oxygen saturation sensor 14 may provide the regional oxygen saturation signal to the controller 16 or to any other suitable processing device to enable evaluation of the patient's autoregulation status. While the depicted oxygen saturation sensor 14 is a regional saturation sensor, the sensor 14 may be a pulse oximetry sensor configured to obtain the patient's oxygen saturation or may be any suitable sensor configured to provide a signal indicative of the patient's blood flow. For example, the sensor 14 may be configured to emit light at a single wavelength (e.g., an isobestic wavelength) and to provide a signal indicative of blood flow.

In operation, the blood pressure sensor 12 and the oxygen saturation sensor 14 may each be placed on the same or different parts of the patient's body. Indeed, the blood pressure sensor 12 and the oxygen saturation sensor 14 may in some cases be part of the same sensor or supported by a single sensor housing. For example, the blood pressure sensor 12 and the oxygen saturation sensor 14 may be part of an integrated oximetry system configured to non-invasively measure blood pressure (e.g., based on time delays in a PPG signal) and regional oxygen saturation. One or both of the blood pressure sensor 12 or the oxygen saturation sensor 14 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an exemplary system 10 is shown, the exemplary components illustrated in FIG. 1 are not intended to be limiting. Indeed, additional or alternative components and/or implementations may be used.

As noted above, the blood pressure sensor 12 may be configured to provide the blood pressure signal to the controller 16, and the oxygen saturation sensor 14 may be configured to provide the oxygen saturation signal to the controller 16. In certain embodiments, the controller 16 is an electronic controller having electrical circuitry configured to process the various received signals. In particular, the controller 16 may be configured to process the blood pressure signal and the oxygen saturation signal to evaluate the patient's cerebral autoregulation status. Although the blood pressure sensor 12 and the oxygen saturation sensor 14 may be configured to provide their respective signals or data directly to the controller 16, in certain embodiments, the signals or data obtained by the blood pressure sensor 12 and/or the oxygen saturation sensor 14 may be provided to one or more intermediate processing devices (e.g., specialized monitor, such as a blood pressure monitor or an oxygen saturation monitor, or the like), which may in turn provide processed signals or data to the controller 16. In some embodiments, the controller 16 may be part of a specialized monitor, such as a blood pressure monitor, an oxygen saturation monitor, a medical monitor configured to monitor physiological characteristics, or the like.

In the illustrated embodiment, the controller 16 includes a processor 24 and a memory device 26. The controller 16 may also include one or more storage devices. The processor 24 may be used to execute software, such as software for carrying out any of the techniques disclosed herein, such as processing the blood pressure signals and/or oxygen saturation signals, determining changes in the blood pressure signals and/or oxygen saturation signals, comparing the changes to thresholds, determining metrics (e.g., COx) indicative of the patient's autoregulation status, carrying out appropriate actions (e.g., providing indications on a display), and so forth. Moreover, the processor 24 may include multiple microprocessors, one or more "general-purpose" microprocessors, one or more special-purpose microprocessors, and/or one or more application specific integrated circuits (ASICS), or some combination thereof. For example, the processor 24 may include one or more reduced instruction set (RISC) processors.

The memory device 26 may include a volatile memory, such as random access memory (RAM), and/or a nonvolatile memory, such as ROM. The memory device 26 may include one or more tangible, non-transitory, machine-readable media collectively storing instructions executable by the processor 24 to perform the methods and control actions described herein. Such machine-readable media can be any available media that can be accessed by the processor 24 or by any general purpose or special purpose computer or other machine with a processor. The memory device 26 may store a variety of information and may be used for various purposes. For example, the memory device 26 may store processor-executable instructions (e.g., firmware or software) for the processor 24 to execute, such as instructions for carrying out any of the techniques discloses herein, such as processing the blood pressure signal and/or the oxygen saturation signal, determining changes in the blood pressure signals and/or oxygen saturation signals, comparing the changes to thresholds, determining metrics (e.g., COx) indicative of the patient's autoregulation status, carrying out appropriate actions (e.g., providing indications on a display), and so forth. The storage device(s) (e.g., nonvolatile storage) may include read-only memory (ROM), flash memory, a hard drive, or any other suitable optical, magnetic, or solid-state storage medium, or a combination thereof. The storage device(s) may store data (e.g., the blood pressure signal, the oxygen saturation signal, the COx, etc.), instructions (e.g., software or firmware for processing the blood pressure signal and/or the oxygen saturation signal, determining changes in the blood pressure signals and/or oxygen saturation signals, comparing the changes to thresholds, determining metrics (e.g., COx), carrying out appropriate actions, and so forth), predetermined thresholds, and any other suitable data.

As shown, the system 10 includes the output device 18. In some embodiments, the controller 16 may be configured to provide signals indicative of the patient's autoregulation status to the output device 18. As discussed in more detail below, the controller 16 may be configured to generate an alarm signal indicative of the patient's autoregulation status and to provide the alarm signal to the output device 18. The output device 18 may include any device configured to receive signals (e.g., the signal indicative of the patient's autoregulation status, the alarm signal, or the like) from the controller 16 and visually and/or audibly output information indicative of the patient's autoregulation status (e.g., the COx, prior COx values, the COx signal, an alarm, a symbol, a text message, or the like). For instance, the output device 18 may include a display configured to provide a visual representation of the patient's autoregulation status and/or the COx, as determined by the controller 16. Additionally or alternatively, the output device 18 may include an audio device configured to provide sounds in accordance with the patient's autoregulation status and/or the COx. The output device 18 may be any suitable device for conveying such information, including a computer workstation, a server, a desktop, a notebook, a laptop, a handheld computer, a mobile device, or the like. In some embodiments, the controller 16 and the output device 18 may be part of the same device or supported within one housing (e.g., a computer or monitor).

As noted above, in some embodiments, the controller 16 may be configured to determine a cerebral oximetry index (COx) based on the blood pressure signal and the oxygen saturation signal. The controller 16 may derive the COx by determining a linear correlation between blood pressure measurements and oxygen saturation measurements. The linear correlation may be based on a Pearson coefficient, for example. The Pearson coefficient may be defined as the covariance of the measured blood pressure (e.g., mean arterial blood pressure) and oxygen saturation divided by the product of their standard deviations. The result of the linear correlation may be a regression line between oxygen saturation measurements and blood pressure measurements.

Figure 2:
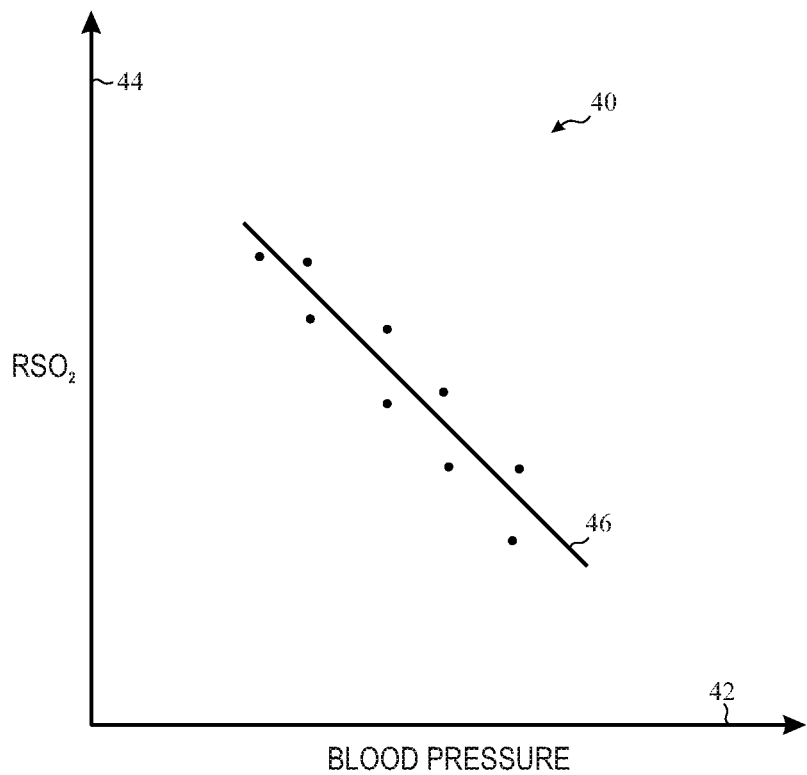
FIG. 2 is an example of a graph illustrating a linear correlation between oxygen saturation values and blood pressure values.

With the foregoing in mind, FIG. 2 is an example of a graph 40 illustrating a linear correlation between blood pressure measurements 42 (e.g., mean arterial blood pressure measurements) and oxygen saturation measurements 44. As noted above, the result of the linear correlation may be a regression line 46 between the blood pressure measurements 42 and the oxygen saturation measurements 44. In the illustrated example, the slope of the regression line 46 is negative and, thus, the COx value is between −1 and 0. When the slope of the regression line 46 is positive, the COx value is between 0 and 1.

During periods of varying blood pressure (e.g., changes of at least approximately 1, 2, 3, 4, or 5 millimeters of mercury [mmHg] over a time window of approximately 0.5, 1, 2, 3, 4, 5, or more minutes), the COx value may provide an accurate and/or useful indication of vascular reactivity, which is related to cerebral blood vessels' ability to control proper blood flow, via vasoconstriction (a narrowing of the blood vessel) and/or vasodilation (expansion of the blood vessel), for example. Thus, in such circumstances, the COx value may also be generally indicative of whether the patient's autoregulation is impaired. For example, in such circumstances, a COx value between −1 and 0 (e.g., a regression line with a relatively flat or negative slope; regional oxygen saturation remains the same or decreases after blood pressure increases) may suggest that cerebral autoregulation is working properly, while a COx value between 0 and 1 (e.g., a regression line with a positive slope; regional oxygen saturation increases after blood pressure increases) or above some predetermined threshold between 0 and 1 (e.g., 0.1, 0.2, 0.3, 0.4, 0.5, 0.6, 0.7, 0.8, or 0.9) may suggest that the cerebral autoregulation is impaired.

Figures 3, 4:
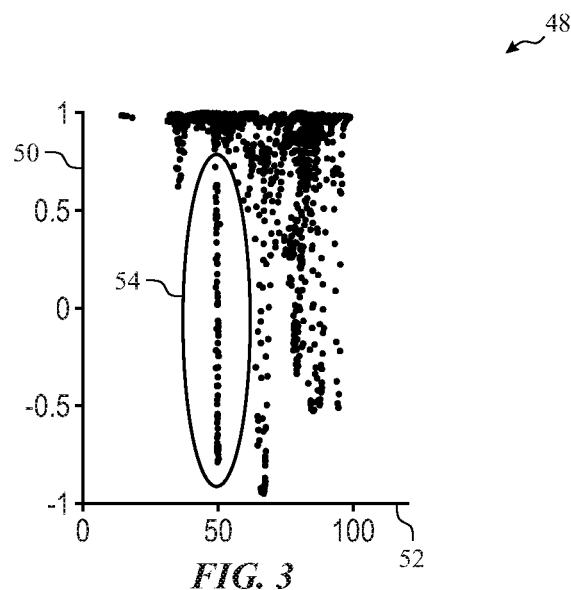
FIG. 3 is an example of a graph illustrating a cerebral oximetry index (COx) over a range of blood pressures.
FIG. 4 is a table illustrating indications of autoregulation status based on various changes in oxygen saturation and blood pressure over a period of time.

However, the COx value may not accurately reflect the patient's autoregulation status when the patient's blood pressure is generally stable (e.g., changes of less than approximately 1, 2, 3, 4, or 5 mmHg over a time window of approximately 0.5, 1, 2, 3, 4, 5, or more minutes). FIG. 3 illustrates a graph 48 of COx values 50 over a range of blood pressures 52. As shown, certain COx values 50 identified by a line 54 are caused by noise due to changes in oxygen saturation during periods of generally stable blood pressure. In certain embodiments of the present disclosure, such COx values 50 (e.g., the COx values 50 within the box 54, or those COx values 50 calculated over a time window in which blood pressure 52 is generally stable) are not calculated, are not used to assess the patient's autoregulation status, and/or are not provided (e.g., are not output to an operator via the output device 18).

Thus, in certain embodiments, the controller 16 may be configured to determine whether the patient's blood pressure varies by more than a threshold (e.g., a blood pressure threshold, such as approximately 1, 2, 3, 4, or 5 mmHg) over a period of time (e.g., a time window of approximately 0.5, 1, 2, 3, 4, 5, or more minutes). In certain embodiments, the controller 16 may calculate the COx only if the patient's blood pressure varies by more than the threshold over the period of time. In certain embodiments, the controller 16 may discard the COx calculated over the period of time and/or may not provide an indication of the COx and/or determine the patient's autoregulation status when blood pressure varies by less than the threshold over the period of time. In certain embodiments, the controller 16 may provide an indication of a prior COx value (e.g., a most recent COx value, a most recent COx value at the same blood pressure, or an average or a weighted average of previously calculated COx values at the same blood pressure) and/or an indication of a prior autoregulation status if the patient's blood pressure varies by less than the threshold over the period of time. For example, the controller 16 may output (e.g., cause display of) the prior COx value until the blood pressure varies by more than the threshold. In some such embodiments, the controller 16 may provide an indication that the COx value and/or autoregulation status is being held, that the prior COx value and/or autoregulation status is being provided, and/or that the COx value and/or the autoregulation status is not being calculated. In some such embodiments, the controller 16 may provide an indication of a time that the prior COx value and/or autoregulation status has been held and/or a time that the COx value and/or the autoregulation status has not been calculated. In some embodiments, the controller 16 may provide an alert if an extended period of time (e.g., more than 5, 10, 15, 20, 30, or more minutes) has passed since the blood pressure has changed by more than the threshold (i.e., since the COx value and/or autoregulation status has been calculated and/or provided). Such an alert may provide an indication of the reliability of the provided COx value and/or autoregulation status. In some embodiments, the controller 16 may be configured to determine and/or to provide an indication of the reliability of the provided COx value and/or autoregulation status. For example, the controller 16 may provide a number (e.g., 1 to 10) or colored indicators indicative of a reliability of the provided COx value and/or autoregulation status based on a length of time since the COx and/or the autoregulation status was calculated. In this way, the changes may enable the controller 16 to identify portions of the COx signal that are adversely affected by noise or processing errors, and which are therefore unreliable. In certain embodiments, the controller 16 may be configured to remove or discard the unreliable portions of the COx signal and/or take other appropriate remedial actions, as discussed in more detail below.

FIG. 4 is a table 60 illustrating indications of autoregulation function that may be provided by the controller 16 based on various changes in oxygen saturation and blood pressure. As shown in rows 62, 64, if the blood pressure changes by more than the threshold over the period of time, the autoregulation status may be determined and/or provided by the controller 16. For example, the controller 16 may calculate the COx based on a relationship between the blood pressure and the oxygen saturation and determine the autoregulation status based on the COx. However, as shown in row 66, if the blood pressure is generally stable over the period of time, the controller 16 may not determine the COx and/or the patient's autoregulation status. As discussed above, in some embodiments, if the blood pressure is generally stable over the period of time, the controller 16 may provide the prior COx and/or autoregulation status.

Figures 5, 6:
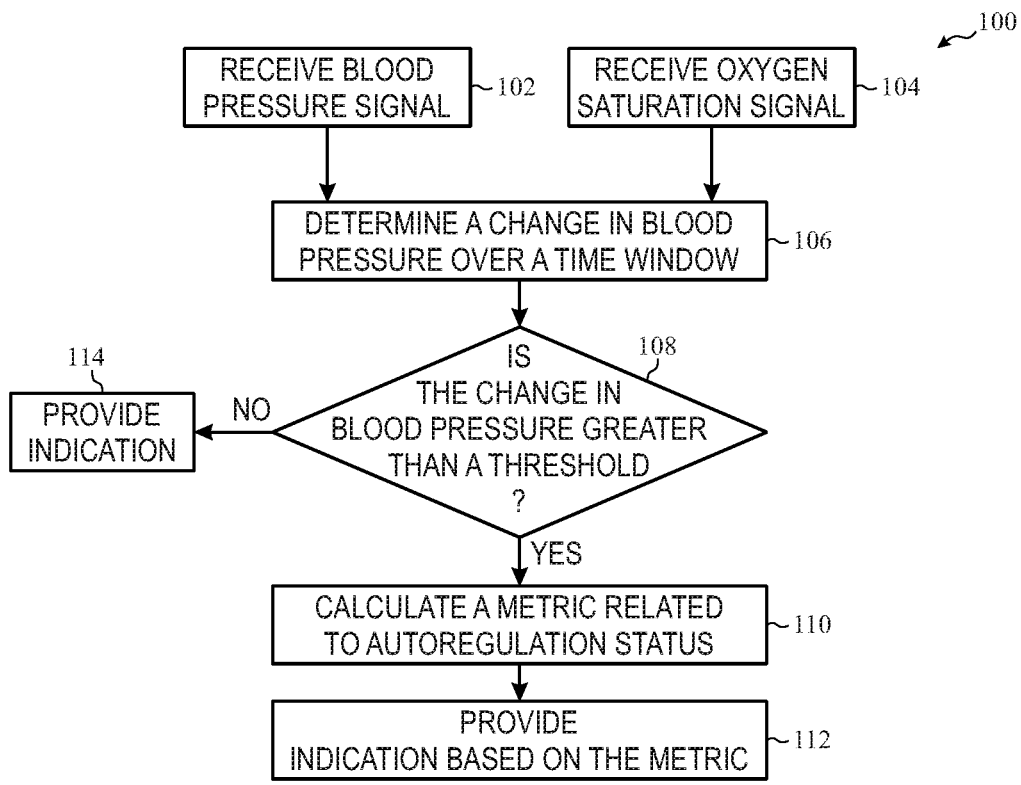
FIG. 5 is another table illustrating indications of autoregulation status based on various changes in oxygen saturation and blood pressure over a period of time.
FIG. 6 is a process flow diagram of a method of monitoring autoregulation by comparing a change in blood pressure to a threshold, in accordance with an embodiment.

In certain embodiments, the controller 16 may be configured to determine and/or to provide information related to the patient's autoregulation status while the patient's blood pressure is generally stable. With the foregoing in mind, FIG. 5 is a table 70 illustrating indications of autoregulation function that may be provided by the controller 16 based on various changes in oxygen saturation and blood pressure. As shown in rows 72, 74, if the blood pressure changes by more than the threshold over the period of time, the autoregulation status may be determined and/or provided by the controller 16. For example, the controller 16 may calculate the COx based on a relationship between the blood pressure and the oxygen saturation and determine the autoregulation status based on the COx. As discussed above, if the blood pressure is generally stable over the period of time, the controller 16 may not determine the COx. However, as shown in boxes 78, 80 of row 76, if the blood pressure is generally stable over the period of time and if the oxygen saturation varies by more than a threshold (e.g., an oxygen saturation threshold, such as approximately 1, 2, 3, 4, or 5 percent) over the period of time, the controller 16 may determine and/or provide an indication that the patient's autoregulation is intact. In certain embodiments, as shown in box 82 of row 76, if both the blood pressure and the oxygen saturation are generally stable over the period of time, the controller 16 may not determine the patient's autoregulation status. In some such cases, the controller 16 may provide the prior autoregulation status or an indication that the patient's autoregulation status has not been determined, for example.

Accordingly, with reference to the system 10 of FIG. 1, in certain embodiments, the controller 16 may determine whether the patient's blood oxygen saturation varies by more than a threshold (e.g., an oxygen saturation threshold, such as approximately 1, 2, 3, 4, or 5 percent) over the period of time. In some embodiments, the controller 16 may determine that the patient's autoregulation is intact if the blood pressure varies by less than the blood pressure threshold and if the oxygen saturation varies by more than the oxygen saturation threshold over the period of time. In certain embodiments, the controller 16 may be configured to provide an indication (e.g., via a display or a speaker) that the patient's autoregulation is intact, if the blood pressure varies by less than the threshold and if the oxygen saturation varies by more than the threshold. Such characteristics may indicate that the patient's blood flow (e.g., as indicated by the oxygen saturation signal) does not correlate with or is not driven by the patient's blood pressure, but rather, is controlled by the patient's autoregulation system to maintain appropriate blood flow.

In some embodiments, if the blood pressure varies by less than the threshold and if the oxygen saturation varies by more than the threshold, the controller 16 may automatically extend the period of time (e.g., continue to collect data for an additional 0.5, 1, 2, 3, 4, or 5 minutes) prior to determining and/or providing an indication that the patient's autoregulation is intact. In some embodiments, if the blood pressure varies by less than the threshold and if the oxygen saturation varies by more than the threshold, the controller 16 may provide an indication of the reliability of the provided intact autoregulation status. For example, the controller 16 may determine and/or provide an indication that the intact autoregulation status has a relatively lower reliability due to the absence of a COx value at the generally stable blood pressure, as compared to periods of varying blood pressure. For example, the controller 16 may provide a number (e.g., 1 to 10) or colored indicator indicative of a reliability of the provided autoregulation status. In some embodiments, if the blood pressure varies by less than the threshold and if the oxygen saturation varies by less than the threshold (i.e., both parameters are generally stable), the controller 16 may provide an indication that the COx and/or the autoregulation status cannot be reliably determined and/or may provide an indication of a prior COx value and/or a prior autoregulation status, in the manner discussed above.

In some embodiments, if the blood pressure varies by less than the threshold and if the oxygen saturation varies by more than the threshold, the controller 16 may compare changes in the patient's regional oxygen saturation signal ($rSO_2$) and arterial oxygen saturation signal ($SpO_2$), and the controller 16 may block output of the indication that patient's autoregulation is intact if both the patient's rSO2 and the SpO2 change by a threshold amount in the same direction (e.g., both increase or both decrease) over the period of time. It should be understood that the thresholds and/or the period of time may be predetermined (e.g., stored in the memory device 26 and accessed by the processor 24) and/or may be selected by a user (e.g., via inputs communicatively coupled to the controller 16). Additionally, although certain examples provided herein utilize the COx, in some embodiments, the techniques may be adapted for use with other metrics or measures of autoregulation, such as a mean velocity index (Mx) and/or a pressure reactivity index (PRx) and/or a vascular reactivity index (HVx) and/or a gradient-based metric, which is discussed in more detail below.

Figure 7:
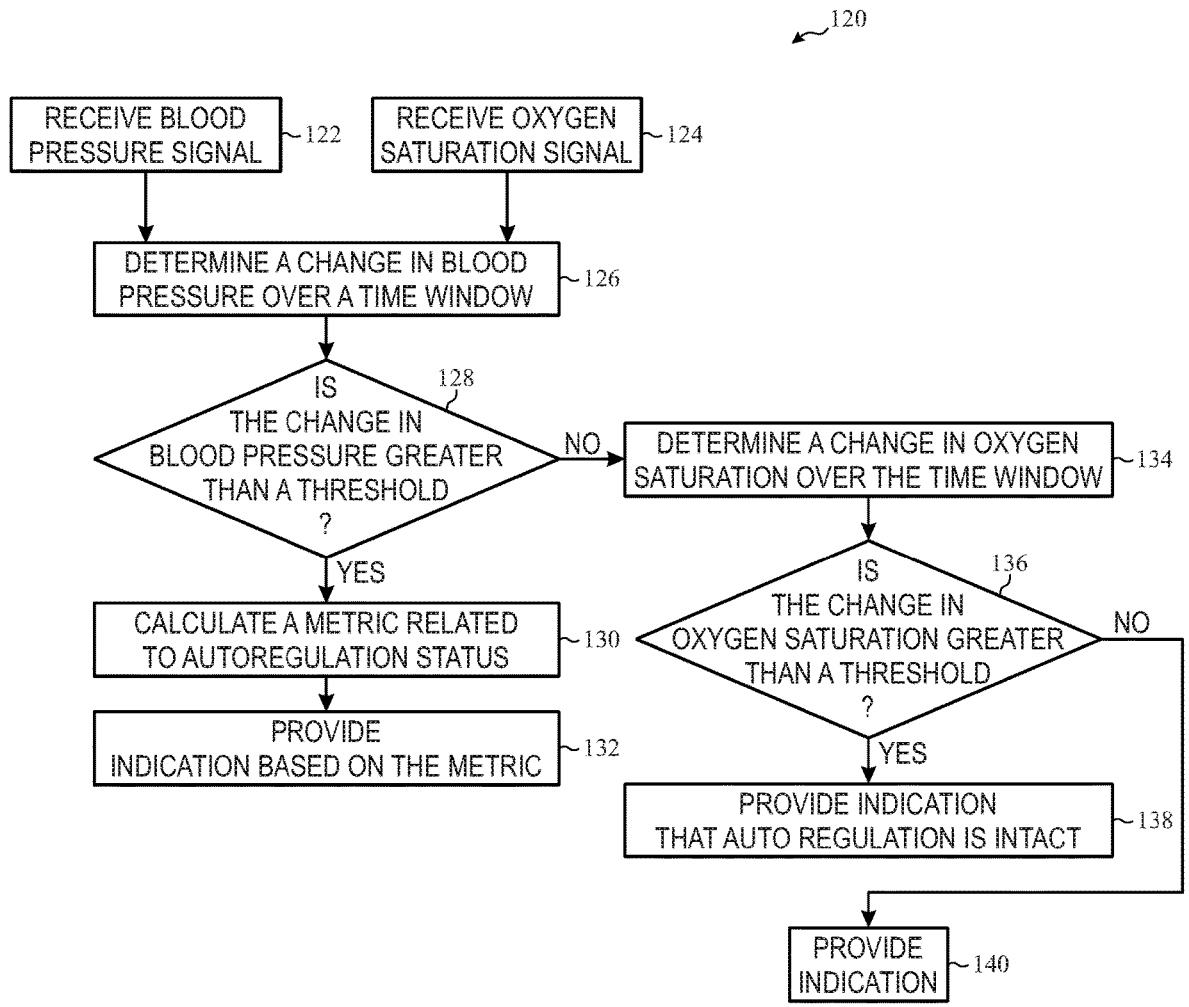
FIG. 7 is a process flow diagram of a method of monitoring autoregulation by comparing a change in blood pressure and a change in oxygen saturation to respective thresholds, in accordance with an embodiment.

FIGS. 6 and 7 are flow charts illustrating methods for monitoring autoregulation based on a change in blood pressure and/or a change in oxygen saturation, in accordance with the present disclosure. The methods disclosed herein include various steps represented by blocks. It should be noted any of the methods provided herein may be performed as an automated procedure by a system, such as system 10. In particular, some or all of the steps of the methods may be implemented by the controller 16 (e.g., the processor 24 of the controller 16) of FIG. 1, for example, to determine the patient's autoregulation status and/or to take an appropriate action (e.g., output a visual or audible indication of the autoregulation status, or the like). Although the flow charts illustrate the steps in a certain sequence, it should be understood that the steps may be performed in any suitable order and certain steps may be carried out simultaneously, where appropriate. Additionally, steps of the various methods disclosed herein may be combined in any suitable manner and steps may be added or omitted. Further, certain steps or portions of the methods may be performed by separate devices. For example, a first portion of a method may be performed by the controller 16, while a second portion of the method may be performed by the sensor 14. In addition, insofar as steps of the methods disclosed herein are applied to received signals, it should be understood that the received signals may be raw signals or processed signals. That is, the methods may be applied to an output of the received signals.

FIG. 6 is a process flow diagram of a method 100 of monitoring autoregulation, in accordance with an embodiment. Some or all of the steps of the method 100 may be implemented by the controller 16 (e.g., the processor 24 of the controller 16) of FIG. 1, for example, to determine the patient's autoregulation status and/or to take an appropriate action (e.g., output a visual or audible indication of the autoregulation status, block calculation and/or output of the COx, or the like). In step 102, the controller 16 may receive the blood pressure signal (e.g., arterial blood pressure signal). In some embodiments, the controller 16 may receive the blood pressure signal from the blood pressure sensor 12, as set forth above. In step 104, the controller 16 may receive the oxygen saturation signal. In some embodiments, the controller 16 may receive the oxygen saturation signal from the oxygen saturation sensor 14, as set forth above.

In step 106, the controller 16 may determine a change in blood pressure over a time window (e.g., approximately 0.5, 1, 2, 3, 4, 5, or more minutes) based on the blood pressure signal. In step 108, the controller 16 may determine whether the change in blood pressure is greater than a threshold (e.g., a blood pressure threshold, such as approximately 1, 2, 3, 4, or 5 mmHg). If the change in blood pressure exceeds the threshold (e.g., in response to a determination that the blood pressure exceeds the threshold), in step 110, the controller 16 may calculate a metric related to autoregulation status, such as the COx. In step 112, the controller 16 may cause the output device 18 to provide a visual or audible indication of the patient's autoregulation status and/or the COx. For example, the controller 16 may cause the output device 18 to provide a numerical, graphical, symbolic, or text message indicative of the patient's autoregulation status and/or the COx.

If the change in blood pressure does not exceed the threshold (e.g., in response to a determination that the blood pressure does not exceed the threshold), in step 114, the controller 16 may provide an appropriate indication via the output device 18. As discussed above, in certain embodiments, the controller 16 may cause the output device 18 to provide an indication of a prior COx value (e.g., a most recent COx value, a most recent COx value at the same blood pressure, or an average or a weighted average of previously calculated COx values at the same blood pressure) and/or an indication of a prior autoregulation status if the patient's blood pressure varies by less than the threshold over the period of time (e.g., in response to a determination that the patient's blood pressure varies by less than the threshold). For example, the controller 16 may output (e.g., cause display of) the prior COx value until the blood pressure varies by more than the threshold. In some such embodiments, the controller 16 may cause the output device 18 to provide an indication that the COx value and/or autoregulation status is being held, that the prior COx value and/or autoregulation status is being provided, and/or that the COx value and/or the autoregulation status is not being calculated.

In some such embodiments, the controller 16 may cause the output device 18 to provide an indication of a time that the prior COx value and/or autoregulation status has been held and/or a time over which the COx value and/or the autoregulation status has not been calculated. In some embodiments, the controller 16 may cause the output device 18 to provide an alert if an extended period of time (e.g., more than 5, 10, 15, 20, 30, or more minutes) has passed since the blood pressure has changed by more than the threshold (i.e., since the COx value and/or autoregulation status has been calculated and/or provided). As noted above, in some embodiments, the controller 16 may be configured to determine and/or to cause the output device 18 to provide an indication of the reliability of the provided COx value and/or autoregulation status.

In some embodiments, in step 114, the controller 16 may cause the output device 18 to provide an appropriate visual or audible indication that the COx and/or the patient's autoregulation status is unavailable. In step 114, the controller 16 may cause the output device 18 to display a blank display screen and/or the controller 16 may discard the COx calculated over the period of time. In some embodiments, the controller 16 may not determine and/or output the COx and/or the patient's autoregulation status if the blood pressure does not change by more than the threshold (e.g., in response to a determination that the blood pressure does not change by more than the threshold).

FIG. 7 is a process flow diagram of a method 120 of monitoring autoregulation, in accordance with an embodiment. Some or all of the steps of the method 120 may be implemented by the controller 16 (e.g., the processor 24 of the controller 16) of FIG. 1, for example, to determine the patient's autoregulation status and/or to take an appropriate action (e.g., output a visual or audible indication of the autoregulation status, block calculation and/or output of the COx, or the like). In step 122, the controller 16 may receive the blood pressure signal (e.g., arterial blood pressure signal). In some embodiments, the controller 16 may receive the blood pressure signal from the blood pressure sensor 12, as set forth above. In step 124, the controller 16 may receive the oxygen saturation signal. In some embodiments, the controller 16 may receive the oxygen saturation signal from the oxygen saturation sensor 14, as set forth above.

In step 126, the controller 16 may determine a change in blood pressure over a time window (e.g., approximately 0.5, 1, 2, 3, 4, 5, or more minutes) based on the blood pressure signal. In step 128, the controller 16 may determine whether the change in blood pressure is greater than a threshold (e.g., a blood pressure threshold, such as approximately 1, 2, 3, 4, or 5 mmHg). If the change in blood pressure exceeds the threshold (e.g., in response to a determination that the change in blood pressure exceeds the threshold), in step 130, the controller 16 may calculate a metric related to autoregulation status, such as the COx. In step 132, the controller 16 may cause the output device 18 to provide a visual or audible indication of the patient's autoregulation status and/or the COx. For example, the controller 16 may cause the output device 18 to provide a numerical, graphical, symbolic, or text message indicative of the patient's autoregulation status and/or the COx.

If the change in blood pressure does not exceed the threshold (e.g., in response to a determination that the change in blood pressure does not exceed the threshold), in step 134, the controller 16 may determine a change in oxygen saturation over the time window (e.g., approximately 0.5, 1, 2, 3, 4, 5, or more minutes) based on the oxygen saturation signal. In step 136, the controller 16 may determine whether the change in oxygen saturation is greater than a threshold (e.g., an oxygen saturation threshold, such as approximately 1, 2, 3, 4, or 5 percent). If the change in oxygen saturation exceeds the threshold (e.g., in response to a determination that the change in oxygen saturation exceeds the threshold), the controller 16 may determine and/or provide an indication via the output device 18 that that patient's autoregulation function is intact. Thus, in some embodiments, the controller 16 may determine and/or cause output of the patient's autoregulation status without correlating the physiological signals (e.g., the blood pressure signal and the oxygen saturation signal) and/or calculating a metric, such as the COx.

In some embodiments, if the blood pressure varies by less than the threshold and if the oxygen saturation varies by more than the threshold (e.g., in response to such determinations), the controller 16 may automatically extend the period of time (e.g., continue to collect data for an additional 0.5, 1, 2, 3, 4, or 5 minutes) prior to determining and/or providing an indication that the patient's autoregulation is intact, in step 138. In some embodiments, if the blood pressure varies by less than the threshold and if the oxygen saturation varies by more than the threshold (e.g., in response to such determinations), the controller 16 may cause the output device 18 to provide an indication of the reliability of the provided intact autoregulation status, as discussed above. In some embodiments, if the blood pressure varies by less than the threshold and if the oxygen saturation varies by more than the threshold (e.g., in response to such determinations), the controller 16 may compare changes in the patient's regional oxygen saturation signal (rSO$_2$) and arterial oxygen saturation signal (SpO$_2$), and the controller 16 may block output of the indication that patient's autoregulation is intact if both the patient's rSO2 and the SpO2 change by a threshold amount in the same direction (e.g., both increase or both decrease) over the period of time.

In some embodiments, if the blood pressure varies by less than the threshold and if the oxygen saturation varies by less than the threshold (i.e., both parameters are generally stable) (e.g., in response to such determinations), the controller 16 may cause the output device 18 to provide an indication, in step 140. In some such embodiments, the controller 16 may cause the output device 18 to provide an indication that the COx and/or the autoregulation status cannot be reliably determined and/or may cause the output device 18 to provide an indication of a prior COx value and/or a prior autoregulation status, in the manner discussed above. In some such embodiments, the controller 16 may cause the output device 18 to provide an indication that the COx value and/or autoregulation status is being held, that the prior COx value and/or autoregulation status is being provided, and/or that the COx value and/or the autoregulation status is not being calculated, for example.

As noted above, some existing systems for monitoring autoregulation may determine a patient's autoregulation status based on a correlation coefficient, such as a cerebral oximetry index (COx), a hemoglobin volume index (HVx), a mean velocity index (Mx), and/or a pressure reactivity index (PRx). However, because many data points are required to reliably calculate such correlation coefficients, an extended period of time may pass before such systems are able to provide an indication of the patient's autoregulation status. For example, some such existing systems collect oxygen saturation data and blood pressure data over a long time window (e.g., approximately 300 seconds or more) before calculating and/or outputting a COx value indicative of the patient's autoregulation status. Furthermore, multiple COx values are typically required to generate a full picture of the patient's autoregulation function (e.g., identify zones of blood pressures at which the patient's autoregulation system functions properly or improperly), and thus, the long time window may cause substantial delays in providing an indication of the patient's autoregulation function. The long time window may also limit the system's ability to promptly identify changes in the patient's autoregulation status or function.

Thus, in accordance with some embodiments of the present disclosure, a patient's autoregulation may be monitored by analyzing a relationship between a change (e.g., gradient) in the patient's blood pressure (e.g., arterial blood pressure) and a change (e.g., gradient) in the patient's oxygen saturation (e.g., regional oxygen saturation) over a period of time (e.g., less than or approximately 30, 40, 50, 60, 90, 120, or 180 seconds). For example, an intact autoregulation system will adjust cerebral blood flow such that the patient's oxygen saturation does not trend with (e.g., change in the same direction as) a change in the patient's blood pressure. However, an impaired autoregulation system may not adequately adjust cerebral blood flow in response to a change in the patient's blood pressure, and thus, a change in the patient's oxygen saturation trends with the change in the patient's blood pressure. Thus, in some embodiments, the controller 16 may be configured to process the blood pressure signal and the oxygen saturation signal to determine respective gradients of the signals (i.e., the blood pressure gradient and the oxygen saturation gradient) over a period of time and to determine the patient's autoregulation status based on the respective gradients.

With reference to FIG. 4, the table 60 illustrates various oxygen saturation gradients and blood pressure gradients and corresponding autoregulation statuses. As shown in rows 62, 64, the patient's autoregulation system may be impaired if the blood pressure gradient and the oxygen saturation gradient trend together (e.g., change in the same direction) over the period of time. In some cases, the patient's autoregulation system may be intact if the blood pressure gradient and the oxygen saturation gradient do not trend together (e.g., do not change in the same direction, such as change in different directions, or the blood pressure changes while the oxygen saturation remains generally stable) over the period of time.

In some embodiments, as shown in row 66, if the blood pressure is generally stable over the period of time, the patient's autoregulation status may not be reliably determined. As discussed with respect to the table 70 of FIG. 5, it should be understood that in some embodiments, if the blood pressure is generally stable over the period of time and the oxygen saturation changes over the period of time, the patient's autoregulation system may be intact because the patient's blood changes independently of blood pressure (i.e., is not driven by changes in blood pressure).

Thus, the controller 16 may be configured to receive and to process the blood pressure signal and the oxygen saturation signal, determine the blood pressure gradient and the oxygen saturation gradient over a period of time, and determine the patient's autoregulation status based on the gradients. In some embodiments, the controller 16 may be configured to determine that the patient's autoregulation system is impaired if the gradients trend together and to determine that patient's autoregulation system is intact if the gradients do not trend together.

In some embodiments, the controller 16 may be configured to consider additional factors, such as whether an absolute value of the blood pressure gradient exceeds a threshold (e.g., a blood pressure gradient threshold) and/or whether an absolute value of the oxygen saturation gradient exceeds a threshold (e.g., an oxygen saturation gradient threshold). In some such cases, the controller 16 may only determine the patient's autoregulation status if the absolute value of the blood pressure gradient exceeds the threshold. In some embodiments, the controller 16 may be configured to determine that the patient's autoregulation system is impaired if the gradients trend together and if the respective absolute value of each gradient exceeds a respective threshold. In some embodiments, the controller 16 may be configured to determine that the patient's autoregulation system is intact if the blood pressure gradient and the oxygen saturation gradient do not trend together (e.g., the respective absolute value of each gradient exceeds a respective threshold and the gradients are in different directions, the absolute value of the blood pressure gradient exceeds the threshold and the absolute value of the oxygen saturation gradient does not exceed the threshold, and/or the absolute value of the blood pressure gradient does not exceed the threshold and the absolute value of the oxygen saturation gradient exceeds the threshold).

Figure 8:
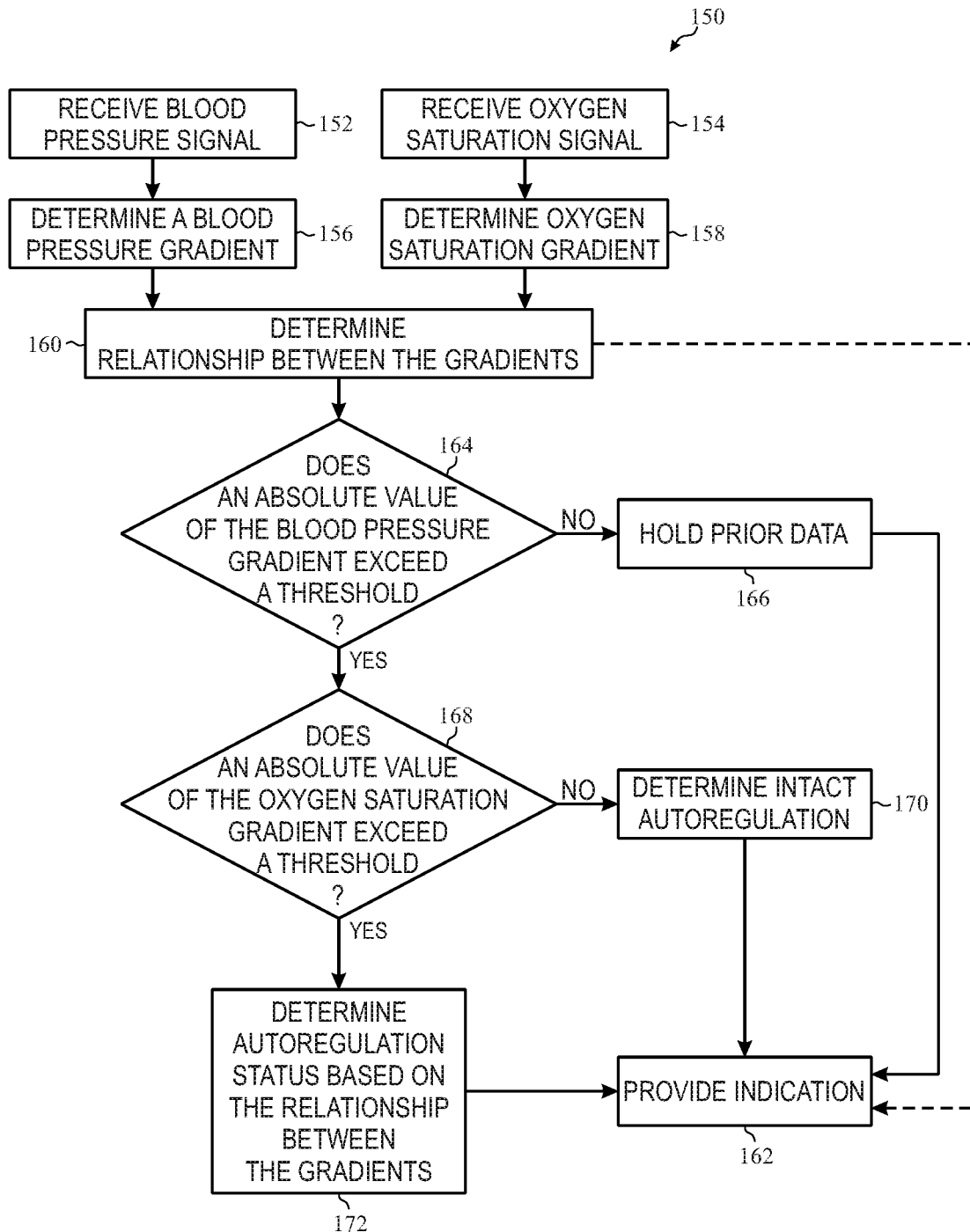
FIG. 8 is a process flow diagram of a method of monitoring autoregulation based on a relationship between gradients of oxygen saturation and blood pressure, in accordance with an embodiment.

With the foregoing in mind, FIG. 8 is a flow chart illustrating a method 150 for monitoring autoregulation based on a relationship between gradients of oxygen saturation and blood pressure (e.g., gradient-based metric), in accordance with the present disclosure. As shown in FIG. 8, in step 152, the controller 16 may receive the blood pressure signal (e.g., arterial blood pressure signal). In some embodiments, the controller 16 may receive the blood pressure signal from the blood pressure sensor 12, as set forth above. In step 154, the controller 16 may receive the oxygen saturation signal. In some embodiments, the controller 16 may receive the oxygen saturation signal from the oxygen saturation sensor 14, as set forth above.

In step 156, the controller 16 may determine a blood pressure gradient over a period of time (e.g., a time window of less than or approximately 30, 40, 50, 60, 90, 120, or 180 seconds) based on the blood pressure signal. In step 158, the controller 16 may determine an oxygen saturation gradient (e.g., a change in oxygen saturation) over the period of time based on the oxygen saturation signal. In step 160, the controller 16 may determine a relationship between the blood pressure gradient and the oxygen saturation gradient. For example, the controller 16 may determine whether the gradients trend together (e.g., whether both gradients are negative or positive) over the period of time. As discussed above, gradients that trend together may be indicative of impaired autoregulation status, while gradients that do not trend together may be indicative of intact autoregulation status.

In some embodiments, as shown in a dotted line, in step 162, the controller 16 may be configured to instruct the output device 18 to provide an indication of the patient's autoregulation status based on the relationship between the blood pressure gradient and the oxygen saturation gradient. For example, the controller 16 may instruct the output device 18 to provide an indication that the patient's autoregulation status is impaired if the gradients trend together and/or an indication that the patient's autoregulation status is intact if the gradients do not trend together. In some embodiments, the output device 18 includes a display to display a text message, a symbol, or other visual representation of the patient's autoregulation status and/or the output device 18 includes a speaker to provide sounds in accordance with the patient's autoregulation status.

As discussed above, in certain embodiments, the controller 16 may be configured to consider additional factors to determine the patient's autoregulation status and/or prior to outputting the indication. As shown, in certain embodiments, the controller 16 may compare the change in blood pressure and the change in oxygen saturation to respective thresholds to determine the patient's autoregulation status. For example, in step 164 of the illustrated method 150, the controller 16 may determine whether an absolute value of the blood pressure gradient over the period of time exceeds a threshold (e.g., a predetermined threshold, such as 0.1, 0.5, 1, 2, 3, 4, 5, or more mmHg). In step 166, if the absolute value of the blood pressure gradient does not exceed the threshold (e.g., in response to a determination that the absolute value of the blood pressure gradient does not exceed the threshold), the controller 16 may not determine and/or output the patient's autoregulation status based on the gradients over the current period of time, but instead may hold a prior determination (e.g., an autoregulation status determined in a prior time window and/or at a similar blood pressure). In step 162, the controller 16 may instruct the output device 18 to provide an autoregulation status indication based on the prior determination. In some embodiments, the controller 16 may instruct the output device 18 to provide an indication that the patient's autoregulation status could not be reliably determined and/or that the prior determination is provided on the output device 18.

If the absolute value of the blood pressure gradient exceeds the threshold (e.g., in response to a determination that the absolute value of the blood pressure gradient exceeds the threshold), the controller 16 may determine whether an absolute value of the oxygen saturation gradient over the period of time exceeds a threshold (e.g., predetermined threshold, such as 0.1, 0.5, 1, 2, 3, 4, 5, or more percent), in step 168. In some such embodiments, if the absolute value of the oxygen saturation gradient does not exceed the threshold (e.g., in response to a determination that the absolute value of the oxygen saturation gradient does not exceed the threshold), the controller 16 may determine that the patient's autoregulation system is intact, in step 170. Following such a determination, the controller 16 may instruct the output device 18 to provide an indication that the patient's autoregulation status is intact, in step 162.

In step 172, if the absolute value of the blood pressure gradient and the absolute value of the oxygen saturation gradient exceed the respective thresholds (e.g., in response to such determinations), the controller 16 may determine the patient's autoregulation status (e.g., impaired or intact) based on the relationship between the gradients determined in step 160, and the controller 16 may instruct the output device 18 to provide an output indicative of the patient's autoregulation status based on the relationship between the gradients, in step 162. In such cases, the controller 16 may instruct the output device 18 to provide an indication that the patient's autoregulation status is impaired if the gradients trend together and/or an indication that the patient's autoregulation status is intact if the gradients do not trend together. As noted above with respect to FIG. 5, in some embodiments, if the blood pressure gradient does not exceed the threshold and the oxygen saturation gradient exceeds the threshold over the period of time (e.g., in response to such determinations), the controller 16 may be configured to determine that the patient's autoregulation system is intact and/or to instruct the output device 18 to provide an indication.

Figure 9C:
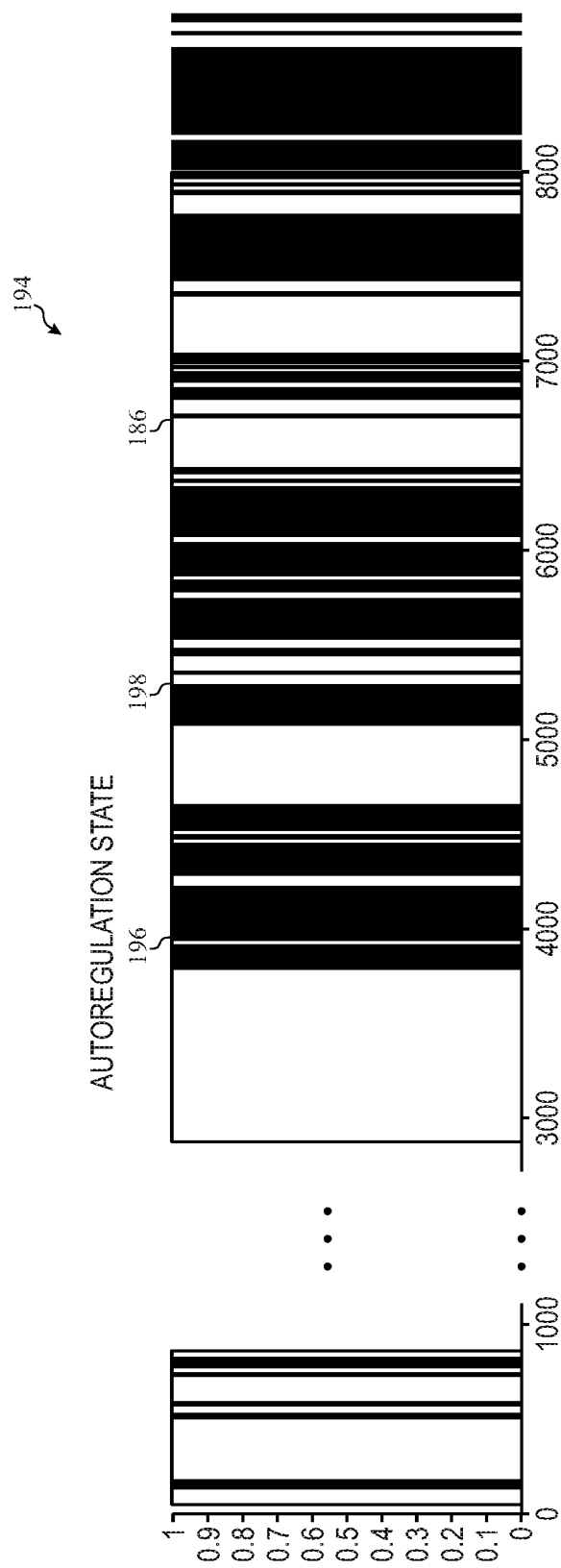
FIG. 9C is an example of a graph illustrating autoregulation status over the period of time based on the gradients of FIG. 9B.

FIG. 9A is an example of a graph 180 illustrating an oxygen saturation signal 182 and a blood pressure signal 184 over a period of time 186. FIG. 9B is an example of a graph 188 illustrating an oxygen saturation gradient 190 (e.g., a gradient of the oxygen saturation signal 182) and a blood pressure gradient 192 (e.g., a gradient of the blood pressure signal 184) over the period of time 186. As discussed above, the controller 16 may be configured to receive the oxygen saturation signal 182 and the blood pressure signal 184 and determine respective gradients 190, 192 over the period of time 186. The relationship between the gradients 190, 192 may be indicative of the patient's autoregulation status and may be used to generate an indication, such as visual or audible indication, of the patient's autoregulation status via the output device 18. For example, FIG. 9C is an example of a graph 194 illustrating a representation of the patient's autoregulation status over the period of time 186 based on the gradients of FIG. 9B. In the illustrated embodiment, the lighter colored regions 196 represent intact autoregulation and the darker colored regions 198 represent impaired autoregulation. In some embodiments, the graph 194 may be provided for visualization by an operator via a display of the output device 18.

In some embodiments, the controller 16 may be configured to determine a confidence level (e.g., quality metric) associated with the determined autoregulation status. In some embodiments, the confidence level may vary based on the absolute value of one or both gradients. In general, greater absolute values over the period of time may correspond to greater confidence in the determined autoregulation status. For example, if the patient's blood pressure and oxygen saturation both change substantially in the same direction over the period of time, the confidence in the determination that the patient's autoregulation function is impaired is generally higher than if the blood pressure and oxygen saturation both change in the same direction by a smaller absolute value. The controller 16 may be configured to determine and to assign a confidence level (e.g., numerical value on a scale, such as a scale of 1 to 10 or 1 to 100, or a non-numerical indicator, such as high, intermediate, or low) based on the absolute values of the gradients, such as based on whether the absolute values of the gradients exceed various thresholds. In some embodiments, the controller 16 may be configured to instruct the output device 18 to provide a visual or audible indication of the confidence level (e.g., the numerical value or non-numerical indicator).

Additionally or alternatively, in some embodiments, a correlation coefficient or a significance value (p value) of a fitted line used to calculate the blood pressure gradient or the oxygen saturation gradient in the period of time may be used as a confidence metric. In particular, the p value may enable the controller 16 to determine whether the gradients are reliable or unreliable. For example, the p value may enable the controller 16 to identify certain portions of the signals that are adversely affected by noise, and therefore, unreliable. In some embodiments, the controller 16 maybe configured to calculate the p value and to remove unreliable data based on the p value.

Additionally or alternatively, in some embodiments, the confidence level may be determined and/or adjusted based on prior gradients and/or prior autoregulation status determinations (e.g., in prior periods of time or prior time windows). For example, respective gradients across the same blood pressures over multiple time windows may be compared and used to determine whether the gradients and/or autoregulation status determination in the current time window agree with the prior gradients and/or prior autoregulation status determinations. If the information agrees, the confidence level may be high or increased, while if the information does not agree, the confidence level may be low or decreased. In some embodiments, the gradients across multiple time windows may be averaged to generate average gradients (e.g., an average blood pressure gradient and an average oxygen saturation gradient), and the average gradients may be used to determine the patient's autoregulation status in the manner set forth above with respect to FIGS. 1-9. Additional techniques for processing and/or considering information across multiple time windows are discussed in more detail below.

In some embodiments, the controller 16 may be configured to determine the patient's autoregulation status without calculating a correlation coefficient, such as a COx, HVx, Mx, and/or PRx. In some embodiments, the controller 16 may be configured to determine the patient's autoregulation status based on the gradients over the period of time in combination with one or more correlation coefficients calculated simultaneously or at different times. For example, the controller 16 may be configured to utilize the gradients at the beginning of a monitoring session (e.g., during first 30, 40, 50, 60, 90, 120, or 180 seconds of the signals) to quickly provide an indication of the patient's autoregulation status, and then subsequently calculate and utilize the COx in addition to or in lieu of the gradients. Such embodiments may advantageously enable efficient determination and output of an indication of the patient's autoregulation status at the beginning of the patient monitoring session without the extended delay that may occur in typical systems that determine autoregulation status based only on the correlation coefficients. Furthermore, when the gradients are used in conjunction with one or more correlation coefficients, the combination of measurements may enable the controller 16 to quickly identify sudden changes in the patient's autoregulation status and/or provide increased confidence in the determination of the patient's autoregulation status.

The patient's autoregulation status may be monitored over multiple time windows and across various blood pressures, and this information may be used to generate a full picture of the patient's autoregulation function. In general, a patient's autoregulation system may typically function well over a certain range of blood pressures. Accordingly, each patient typically exhibits at least three autoregulation zones: a lower impaired autoregulation zone associated with relatively low blood pressures at which the patient's autoregulation function is impaired, an intact autoregulation zone associated with intermediate blood pressures at which the patient's autoregulation system works properly, and an upper impaired autoregulation zone associated with relatively high blood pressures at which the patient's autoregulation function is impaired. For example, although the blood pressures at which the autoregulation system functions properly may vary by patient, a particular patient may exhibit a lower impaired autoregulation zone associated with relatively low blood pressures of less than approximately 60 mmHg at which the patient's autoregulation function is impaired, an intact autoregulation zone associated with intermediate blood pressures between approximately 60 and 150 mmHg at which the patient's autoregulation system works properly, and an upper impaired autoregulation zone associated with relatively high blood pressures above approximately 150 mmHg at which the patient's autoregulation function is impaired.

In some embodiments of the present disclosure, the controller 16 may determine a current instantaneous autoregulation status, S(i), for each blood pressure value based on the relationship between the blood pressure gradient and the oxygen saturation gradient in a time window, such as in the manner set forth above with respect to FIGS. 8 and 9, for example. In some embodiments, the controller 16 may determine a confidence level of the current instantaneous autoregulation status. The current instantaneous autoregulation status and/or the confidence level of the current instantaneous autoregulation status may be stored, such as in the memory 26.

For each blood pressure, the current instantaneous autoregulation status, S(i), and a previously reported instantaneous autoregulation status, rS(i−1), are considered together by the controller 16 to generate an updated autoregulation status, rS(i), which may then be reported to the output device 18 to provide an indication of the patient's current autoregulation status. Thus, the current instantaneous autoregulation status, S(i), may be modified, adjusted, or discarded in view of prior data and/or prior autoregulation status determination(s).

For example, in certain embodiments, for each blood pressure, the current instantaneous autoregulation status, S(i), may be compared to the previously reported instantaneous autoregulation status, rS(i−1). If S(i) and rS(i−1) agree (e.g., both indicate intact autoregulation or both indicate impaired autoregulation at the blood pressure), then rS(i) is set to S(i) and a high confidence level is assigned to and/or reported (e.g., via the output device 18) with rS(i). If S(i) and rS(i−1) do not agree (e.g., one indicates intact autoregulation and one indicates impaired autoregulation at the blood pressure), then the controller 16 may check a confidence level associated with rS(i−1). If the confidence level associated with rS(i−1) is high (e.g., above a threshold), then rS(i) is set to rS(i−1). If the confidence level associated with rS(i−1) is low (e.g., below the threshold), then the controller 16 may evaluate the previously reported instantaneous autoregulation statuses at neighboring blood pressures and may set rS(i) based on some rS(i) indicators or values previously determined at neighboring blood pressures. For example, if the patient's autoregulation status is impaired at neighboring blood pressures located above and below the current blood pressure, then rS(i) may be set to indicate impaired autoregulation status. In some such embodiments, the confidence level associated with rS(i) may be reduced or set to low.

To facilitate generation of the full picture of the patient's autoregulation function and to facilitate reliable reporting of the patient's autoregulation status across all blood pressures, the autoregulation status and/or corresponding confidence levels at neighboring blood pressures may be considered by the controller 16 in various other situations. In some embodiments, if there is no prior data for a particular blood pressure, if the confidence level of the current instantaneous autoregulation status, S(i), at a particular blood pressure is below a predetermined threshold, and/or if conflicting autoregulation status indications at a particular blood pressure or across nearby blood pressures exist, the controller 16 may consider the previously reported autoregulation statuses at neighboring blood pressures and/or the corresponding confidence levels. For example, if a current instantaneous autoregulation status, S(i), at 100 mmHg indicates that the patient's autoregulation status is impaired, but previously reported instantaneous autoregulation statuses at 95 mmHg and at 105 mmHg indicate intact autoregulation with higher confidence, the controller 16 may discard S(i) and/or set rS(i) to provide an indication of intact autoregulation at 100 mmHg. Thus, the controller 16 may be configured to remove anomalous regions or data.

In some embodiments, if there is no prior data for a particular blood pressure, then the current instantaneous autoregulation status, S(i), will be stored, such as in the memory device 26 or buffer, until a certain number (e.g., 2, 3, 4, 5 or more) of current instantaneous autoregulation statuses, S(i), at the particular blood pressure are determined (e.g., via assessment of the blood pressure gradient and oxygen saturation gradient over multiple time windows). In some embodiments, the controller 16 may not identify or provide an indication that the particular blood pressure is associated with an intact or impaired autoregulation status until at least two S(i) indications at the particular blood pressure are obtained and agree with one another. Additionally or alternatively, in some embodiments, prior data may be down weighted and/or discarded based on age. In some embodiments, a confidence level associated with a previously reported instantaneous autoregulation status, rS(i−1), may be reduced based on age.

Figure 10:
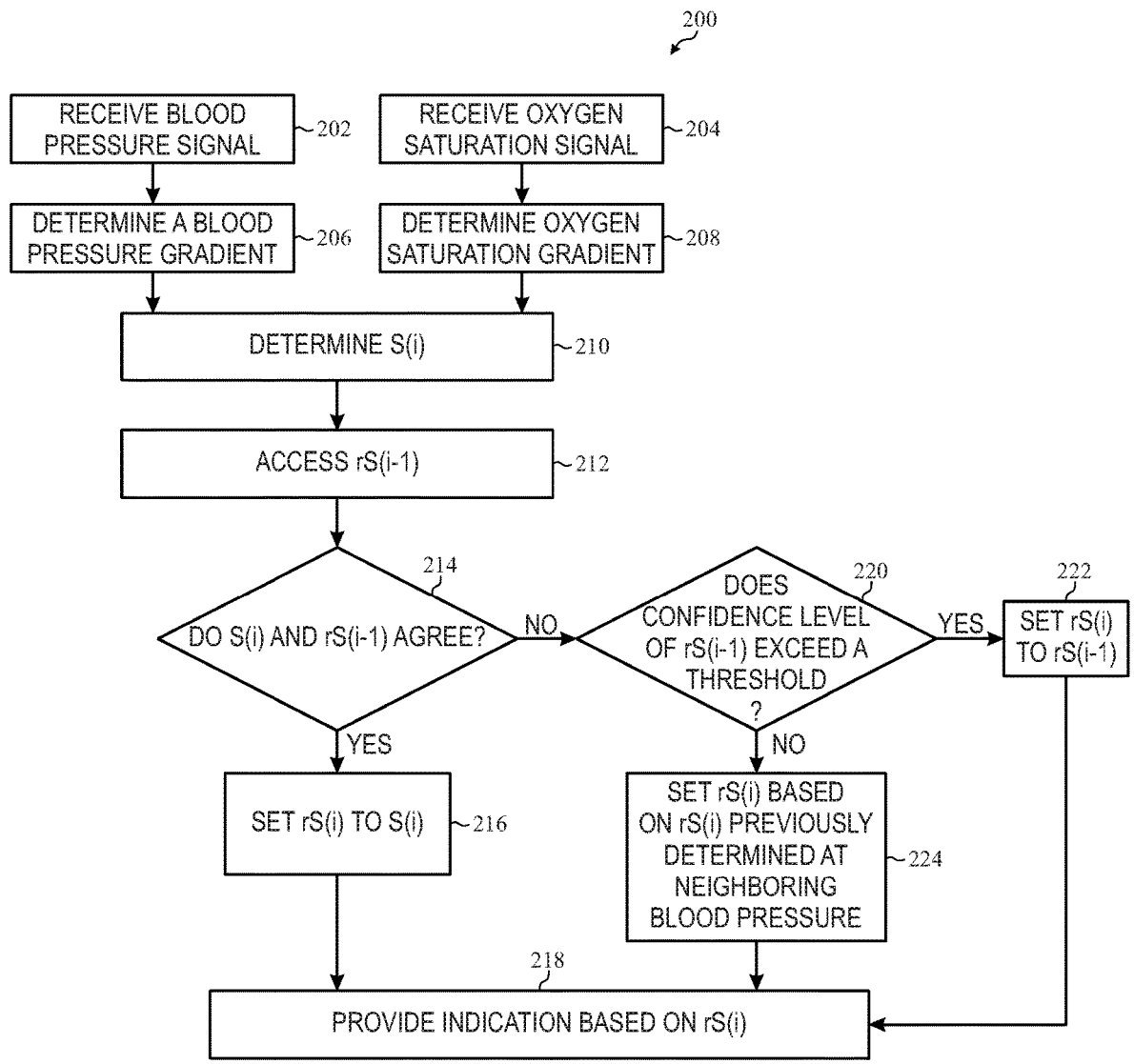
FIG. 10 is a process flow diagram of another method of monitoring autoregulation based on prior autoregulation data, in accordance with an embodiment.

With the foregoing in mind, FIG. 10 is a flow chart illustrating a method 200 for monitoring autoregulation, in accordance with the present disclosure. In step 202, the controller 16 may receive the blood pressure signal (e.g., arterial blood pressure signal). In some embodiments, the controller 16 may receive the blood pressure signal from the blood pressure sensor 12, as set forth above. In step 204, the controller 16 may receive the oxygen saturation signal. In some embodiments, the controller 16 may receive the oxygen saturation signal from the oxygen saturation sensor 14, as set forth above.

In step 206, the controller 16 may determine a blood pressure gradient over a time window (e.g., less than or approximately 30, 40, 50, 60, 90, 120, or 180 seconds) based on the blood pressure signal. In step 208, the controller 16 may determine an oxygen saturation gradient (e.g., a change in oxygen saturation) over the time window based on the oxygen saturation signal. In step 210, the controller 16 may determine the patient's autoregulation status based on a relationship between the blood pressure gradient and the oxygen saturation gradient in the manner described above with respect to FIGS. 8 and 9, for example. In certain embodiments, for each blood pressure in the time window, the controller 16 may set a current instantaneous autoregulation status, S(i), to intact or impaired based on the relationship between the gradients and/or may assign a corresponding confidence level.

In step 212, the controller 16 may access a previously reported instantaneous autoregulation status, rS(i−1), which may be stored in the memory device 26, for example. In step 214, for each blood pressure, the current instantaneous autoregulation status, S(i), is compared to the previously reported instantaneous autoregulation status, rS(i−1), by the controller 16. In step 216, if S(i) and rS(i−1) agree (e.g., in response to a determination that both indicate intact autoregulation or both indicate impaired autoregulation at the blood pressure), then the controller 16 may generate an updated autoregulation status, rS(i), by setting rS(i) to S(i). In some such embodiments, the controller 16 may assign and/or report a high confidence level (e.g., via the output device 18) with rS(i). In step 218, the controller 16 may instruct the output device 18 to provide an indication of rS(i).

In step 220, if S(i) and rS(i−1) do not agree (e.g., in response to such determination), then the controller 16 may check a confidence level associated with rS(i−1). In step 122, if the confidence level associated with rS(i−1) is high (e.g., in response to a determination that rS(i−1) is above a threshold), then rS(i) is set to rS(i−1) and reported in step 118. In step 224, if the confidence level associated with rS(i−1) is low (e.g., in response to a determination that rS(i−1) is below the threshold), then the controller 16 may evaluate the previously reported instantaneous autoregulation statuses at neighboring blood pressures and may set rS(i) based on the neighboring blood pressures.

As discussed above, various additional post-processing techniques may be applied to determine and report the patient's autoregulation status. For example, the controller 16 may be configured to utilize prior data at neighboring blood pressures in any of a variety of manners, such as to remove anomalous regions. In some embodiments, the controller 16 may not determine or provide an indication of autoregulation status until a minimum number of data points at a given blood pressure are obtained. Thus, according to the method 200 set forth in FIG. 10, the current instantaneous autoregulation status, S(i), determined via analysis of the gradients in the time window may be modified, adjusted, or discarded in view of prior data and/or prior autoregulation status determination(s) at the same or neighboring blood pressures. The updated autoregulation status, rS(i), generated via the method 200 and reported (e.g., via the output device 18) in step 218 may provide a reliable indication of autoregulation status and may facilitate generation of a full picture of the patient's autoregulation function over time. The updated autoregulation status 218 may be stored in the memory device 26 for subsequent use (e.g., to modify future instantaneous autoregulation status(es) in the manner set forth in steps 212-224).

Figure 11:
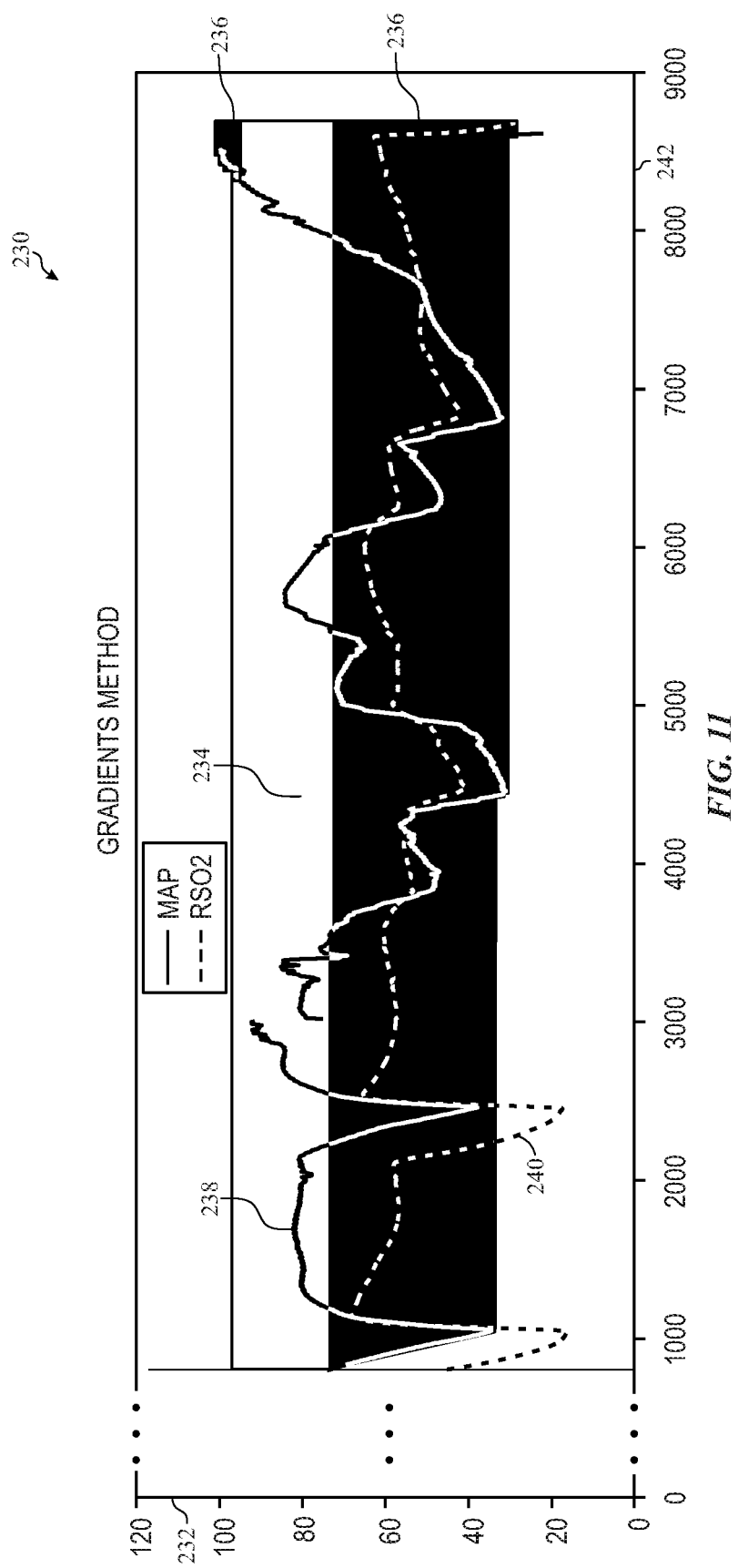
FIG. 11 is an example of a graph that may be generated via the method of FIG. 10, wherein the graph illustrates autoregulation function across various blood pressures.

FIG. 11 is an example of a graph 230 that may be generated via the method 200 of FIG. 10. The graph 230 illustrates autoregulation function across various blood pressures 232. In the illustrated embodiment, the lighter colored region 234 (e.g., blood pressure range) represents an intact autoregulation zone and the darker colored regions 236 (e.g., blood pressure ranges) represent impaired autoregulation zones. To facilitate discussion, the graph 230 also illustrates a blood pressure signal 238 and an oxygen saturation signal 240 obtained over time 242 that were used to generate the graph 230. In some embodiments, the graph 230 may be provided for visualization by an operator via the output device 18. Additionally or alternatively, in some embodiments, the controller 16 may calculate and/or instruct the output device 18 to provide other indications based on the graph 230, such as a numerical indication of an upper limit of autoregulation (ULA) value and/or a lower limit of autoregulation (LLA) that approximately define an upper and a lower blood pressure boundary, respectively, of the intact autoregulation zone (e.g., the lighter color region 234) within which autoregulation is generally intact and functions properly.

As noted above, the method 200 set forth in FIG. 10 may be used to determine the patient's autoregulation status and/or to generate a full picture of the patient's autoregulation function based on various coefficients or indices related to autoregulation, such as COx, Mx, HVx, and PRx. To facilitate discussion, the COx is provided as an example. In some embodiments, the controller 16 may determine a COx value based on the linear correlation between blood pressure measurements of a blood pressure signal and oxygen saturation measurements of an oxygen saturation signal over a period of time (e.g., a time window, such as approximately 300 seconds). As discussed above with respect to FIG. 2, the linear correlation may be based on a Pearson coefficient, which may be defined as the covariance of the measured blood pressure (e.g., mean arterial blood pressure) and oxygen saturation divided by the product of their standard deviations. The result of the linear correlation may be a regression line between oxygen saturation measurements and blood pressure measurements, which is then used to determine the patient's autoregulation status. The controller 16 may determine a value of the COx, which may be between −1 and 1, inclusive, where −1 represents total negative correlation, +1 represents total positive correlation, and 0 represents the absence of correlation between the blood pressure measurements and the oxygen saturation measurements. Thus, COx values between −1 and 0 may suggest that cerebral autoregulation is working properly, while COx values between 0 and 1 may suggest that the cerebral autoregulation is impaired. In some cases, a predetermined threshold between 0 and 1 may be utilized to determine whether the patient's autoregulation is impaired. For example, in some embodiments, the controller 16 may be configured to determine that the patient's autoregulation is impaired when the COx value is greater than 0.1, 0.2, 0.3, 0.4, 0.5, 0.6, 0.7, 0.8, or 0.9.

In some embodiments, the controller 16 may determine a current instantaneous COx value, COx(i), for each blood pressure in the time window. The controller 16 may be configured to adapt steps 212-224 of the method 200 of FIG. 10 to adjust the current instantaneous COx value, COx(i), based on prior COx value(s), rCOx(i−1), to generate an updated COx value, rCOx(i), at the particular blood pressure. For example, the controller 16 may access a prior COx value, compare the current instantaneous COx value to the prior COx value, report the current instantaneous COx value if the current instantaneous COx value and the prior COx value agree (e.g., in response to a determination that both indicate intact autoregulation, both indicate impaired autoregulation, and/or are within a predetermined percentage of one another), report the prior COx value if the current instantaneous COx value and the prior COx value disagree and if the prior COx value has a high confidence level (e.g., above a threshold) (e.g., in response to such determinations), and/or consider the COx values or autoregulation statuses at neighboring blood pressures if the current COx value and the prior COx value disagree and if the prior COx value has a low confidence level (e.g., below the threshold) (e.g., in response to such determinations). The method 200 may be applied to numerical COx values or to status indications (e.g., intact or impaired) based on COx values. For example, COx(i) may be a numerical COx value, such as 0.8, or a status indicator, such as impaired autoregulation status.

In another method 250 set forth in FIG. 7, the current instantaneous COx value, COx(i), may be combined with the previously reported instantaneous COx value, rCOx(i−1), to generate the updated COx value, rCOx(i), for the particular blood pressure. In step 252, the controller 16 may receive the blood pressure signal (e.g., arterial blood pressure signal). In some embodiments, the controller 16 may receive the blood pressure signal from the blood pressure sensor 12, as set forth above. In step 254, the controller 16 may receive the oxygen saturation signal. In some embodiments, the controller 16 may receive the oxygen saturation signal from the oxygen saturation sensor 14, as set forth above.

In step 256, the controller 16 may determine a COx value e.g., between −1 and 1, inclusive) based on the linear correlation between blood pressure measurements of the blood pressure signal and the oxygen saturation measurements of the oxygen saturation signal over a period of time (e.g., a time window, such as approximately 300 seconds), and the controller 16 may set a current instantaneous COx value, COx(i), for each blood pressure in the time window.

In step 258, the controller 16 may access a previously reported instantaneous COx value, rCOx(i−1), which may be stored in the memory device 26, for example. In step 260, the controller 16 may combine COx(i) and rCOx(i−1) for a particular blood pressure to generate an updated COx value, rCOx(i), for the particular blood pressure. In some embodiments, the controller may combine COx(i) and rCOx(i−1) via the following equation:

$$rCO_x(i) = w*CO_x(i) + (1-w)*rCO_x(i-1) \qquad \text{(Equation 1)}$$

where w is a weighting factor. In some embodiments, the weighting factor may be based on a confidence level associated with the COx value. In some embodiments, the weighting factor may be adjusted based on the age of rCOx(i−1).

In step 260, the controller 16 may apply various additional processing techniques to determine and/or report the patient's autoregulation status. For example, if there is no prior data for a particular blood pressure, if the confidence level of the current instantaneous COx value, COx(i), at a particular blood pressure is below a predetermined threshold, and/or if conflicting COx values and/or autoregulation status indications at a particular blood pressure or across nearby blood pressures exist (e.g., in response to such determination(s)), the controller 16 may consider the previously reported COx values and/or autoregulation statuses at neighboring blood pressures and/or the corresponding confidence levels. For example, the controller 16 may be configured to consider such information to remove anomalous data. In some embodiments, the controller 16 may not determine or provide an indication of autoregulation status until a minimum number of data points and/or multiple COx values at a given blood pressure are obtained. In some embodiments, a confidence level and/or the weighting factor associated with a previously reported instantaneous COx value, rCOx(i−1), may be reduced based on age. Additionally, if multiple data points at a particular blood pressure are obtained over the period of time, the data points obtained at the beginning of the period of time may be down weighted, or the period of time over which the data points are collected may vary based on a number of data points at the particular blood pressure to facilitate efficient calculation of COx(i) and rCOx(i) at each blood pressure.

Figure 12:
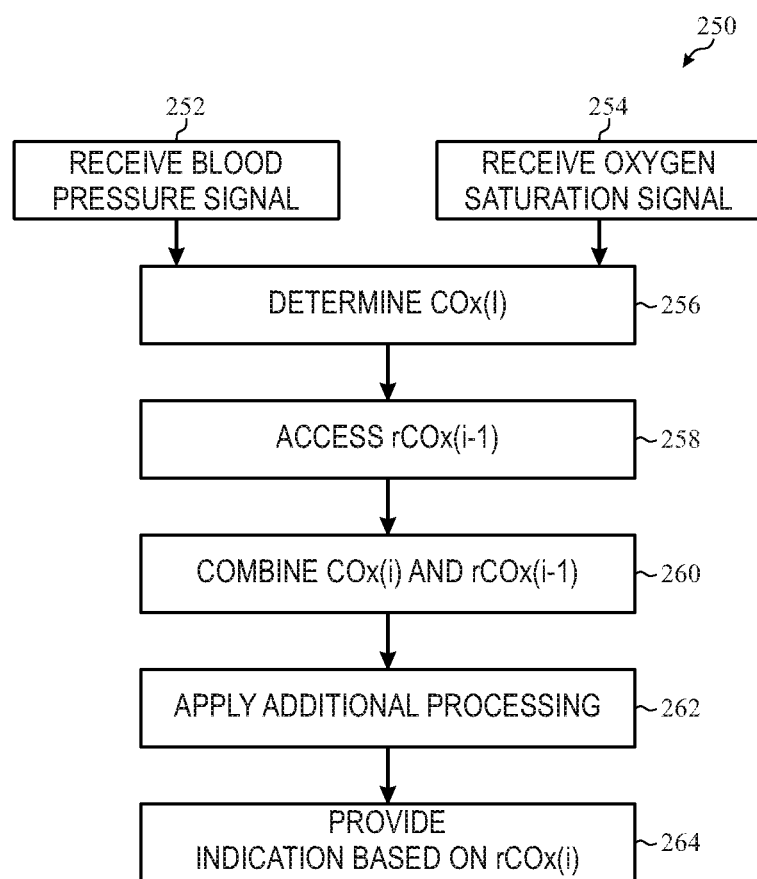
FIG. 12 is a process flow diagram of another method of monitoring autoregulation by updating a correlation coefficient based on prior autoregulation data, in accordance with an embodiment.

In step 262, the controller 16 may instruct the output device 18 to provide an indication of rCOx(i). In some embodiments, the controller 16 may utilize the method 250 to generate a graph similar to the graph 230 shown in FIG. 11 that illustrates autoregulation function across various blood pressures. The controller 16 may instruct the output device 18 to provide the graph or any of a variety of other indications, such as a numerical indication of an upper limit of autoregulation (ULA) value and/or a lower limit of autoregulation (LLA) that approximately define an upper and a lower blood pressure boundary, respectively, of the intact autoregulation zone within which autoregulation is generally intact and functions properly. Thus, according to the method 250 set forth in FIG. 12, the current instantaneous COx value, COx(i), may be modified, adjusted, or discarded in view of prior data and/or prior autoregulation status determination(s) at the same or neighboring blood pressures. The updated autoregulation status, rCOx(i), generated via the method 250 and reported (e.g., via the output device 18) in step 262 may provide a reliable indication of autoregulation status and may facilitate generation of a full picture of the patient's autoregulation function over time.

It should also be understood that the method 250 may be adapted to monitor the patient's autoregulation status with other correlation coefficients, such as HVx, Mx, and/or PRx. Furthermore, the gradients, COx, HVx, Mx, PRx, or any other suitable indicator may be utilized in combination to monitor the patient's autoregulation status. For example, the controller 16 may carry out the method 200 using the gradients and may carry out method 250 using the COx values simultaneously to enable relatively efficient evaluation of the patient's autoregulation status and recognition of changes via the gradients, as well as increased confidence in the determined autoregulation status via the use of multiple measurement techniques. If the autoregulation status determined based on the gradients agrees with the autoregulation status determined based on the COx value, then the confidence level in the determination may be relatively higher than if only one measurement technique were utilized. The confidence level may then be utilized in subsequent calculations or assessments of the patient's autoregulation status in the manner set forth above in FIGS. 10 and 12, thereby increasing the reliability and confidence of the determined autoregulation state, autoregulation zones, and other related information.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A system for monitoring autoregulation, the system comprising:
   an oxygen saturation sensor configured to obtain an oxygen saturation signal indicative of an oxygen saturation of a patient; and
   a controller comprising one or more processors configured to:
      receive the oxygen saturation signal;
      receive a blood pressure signal indicative of a blood pressure of the patient;
      determine an oxygen saturation gradient based on the oxygen saturation signal over a period of time;
      determine a blood pressure gradient based on the blood pressure signal over the period of time;
      determine an absolute value of the blood pressure gradient;
      in response to determining that the absolute value of the blood pressure gradient exceeds a blood pressure gradient threshold in a first instance:
         determine a cerebral oximetry index (COx) value based on the blood pressure signal and the oxygen saturation signal; and
         monitor an autoregulation status of the patient based on the COx value and a relationship between the oxygen saturation gradient and the blood pressure gradient; and
      in response to determining that the absolute value of the blood pressure gradient does not exceed the blood pressure gradient threshold in a second instance, monitor the autoregulation status of the patient based on the relationship between the oxygen saturation gradient and the blood pressure gradient without determining the COx value.

2. The system of claim 1, wherein the one or more processors are configured to:
   determine an absolute value of the oxygen saturation gradient; and
   determine that an autoregulation system of the patient is impaired if the absolute value of the oxygen saturation gradient exceeds an oxygen saturation gradient threshold, if the absolute value of the blood pressure gradient exceeds a blood pressure gradient threshold, and if the oxygen saturation gradient and the blood pressure gradient trend together over the period of time.

3. The system of claim 2, wherein the one or more processors are configured to determine a confidence level associated with the autoregulation status based on the absolute value of the blood pressure gradient, the absolute value of the oxygen saturation gradient, or a combination thereof.

4. The system of claim 1, wherein the one or more processors are configured to present an indication related to the autoregulation status of the patient on a display.

5. The system of claim 1, wherein the one or more processors are configured to determine the autoregulation status without calculating a correlation coefficient between the oxygen saturation signal and the blood pressure signal.

6. The system of claim 1, wherein the one or more processors are configured to:
   set a current instantaneous autoregulation status for a first blood pressure monitored over the period of time based on the determined autoregulation status;

modify the current instantaneous autoregulation status based on a prior instantaneous autoregulation status to generate an updated autoregulation status for the first blood pressure; and
present an indication of the updated autoregulation status via a display.

7. The system of claim 1, wherein the one or more processors are configured to:
determine an absolute value of the oxygen saturation gradient; and
determine that an autoregulation system of the patient is intact if the absolute value of the oxygen saturation gradient exceeds an oxygen saturation gradient threshold over the period of time and if the absolute value of the blood pressure gradient does not exceed a blood pressure gradient threshold over the period of time.

8. A system for monitoring autoregulation, the system comprising:
a memory encoding one or more processor-executable instructions; and
a controller comprising one or more processors configured to access and execute the one or more instructions encoded by the memory, wherein the instructions, when executed cause the one or more processors to:
receive an oxygen saturation signal indicative of an oxygen saturation of a patient;
receive a blood pressure signal indicative of a blood pressure of the patient;
determine an oxygen saturation gradient based on the oxygen saturation signal over a period of time;
determine a blood pressure gradient based on the blood pressure signal over the period of time;
determine an absolute value of the blood pressure gradient;
in response to determining that the absolute value of the blood pressure gradient exceeds a blood pressure gradient threshold in a first instance:
determine a cerebral oximetry index (COx) value based on the blood pressure signal and the oxygen saturation signal; and
monitor an autoregulation status of the patient based on the COx value and a relationship between the oxygen saturation gradient and the blood pressure gradient;
in response to determining that the absolute value of the blood pressure gradient does not exceed the blood pressure gradient threshold in a second instance, monitor the autoregulation status of the patient based on the relationship between the oxygen saturation gradient and the blood pressure gradient without determining the COx value; and
present, via a display, an indication related to the autoregulation status.

9. The system of claim 8, wherein the one or more processors are configured to:
determine an absolute value of the oxygen saturation gradient; and
determine that an autoregulation system of the patient is impaired if the absolute value of the oxygen saturation gradient exceeds an oxygen saturation gradient threshold, if the absolute value of the blood pressure gradient exceeds a blood pressure gradient threshold, and if the oxygen saturation gradient and the blood pressure gradient trend together over the period of time.

10. The system of claim 9, wherein the blood pressure gradient threshold is between two millimeters of mercury (mmHg) and four mmHg.

11. The system of claim 9, wherein the one or more processors are configured to determine a confidence level associated with the autoregulation status based on the absolute value of the blood pressure gradient, the absolute value of the oxygen saturation gradient, or a combination thereof.

12. The system of claim 8, wherein the one or more processors are configured to determine the autoregulation status of the patient without calculating a correlation coefficient between the oxygen saturation signal and the blood pressure signal.

13. The system of claim 8, wherein the one or more processors are configured to:
set a current instantaneous autoregulation status for a first blood pressure monitored over the period of time based on the determined autoregulation status;
modify the current instantaneous autoregulation status based on a prior instantaneous autoregulation status to generate an updated autoregulation status for the first blood pressure; and
present an indication of the updated autoregulation status via the display.

14. The system of claim 13, wherein the one or more processors are configured to:
generate multiple updated autoregulation statuses across multiple blood pressures based on respective modified instantaneous autoregulation statuses; and
generate a graph indicative of the blood pressures at which an autoregulation system of the patient is intact and impaired based on the multiple updated autoregulation statuses.

15. The system of claim 13, wherein the prior instantaneous autoregulation status corresponds to a neighboring blood pressure different from the first blood pressure.

16. The system of claim 8, wherein the one or more processors are configured to:
determine an absolute value of the oxygen saturation gradient; and
determine that an autoregulation system of the patient is intact if the absolute value of the oxygen saturation gradient exceeds an oxygen saturation gradient threshold over the period of time and if the absolute value of the blood pressure gradient does not exceed a blood pressure gradient threshold over the period of time.

17. A method for monitoring autoregulation, the method comprising:
receiving, by one or more processors and from one or more sensors, an oxygen saturation signal indicative of an oxygen saturation of a patient;
receiving, by the one or more processors and from the one or more sensors, a blood pressure signal indicative of a blood pressure of the patient;
determining, by the one or more processors, an oxygen saturation gradient based on the oxygen saturation signal over a period of time;
determining, by the one or more processors, a blood pressure gradient based on the blood pressure signal over the period of time;
determining, by the one or more processors, an absolute value of the blood pressure gradient;
in response to determining that the absolute value of the blood pressure gradient exceeds a blood pressure gradient threshold in a first instance:
determining, by the one or more processors, a cerebral oximetry index (COx) value based on the blood pressure signal and the oxygen saturation signal; and
monitoring, by the one or more processors, an autoregulation status of the patient based on the COx value and a relationship between the oxygen saturation gradient and the blood pressure gradient; and in response to determining that the absolute value of the blood pressure gradient does not exceed the blood pressure gradient threshold in a second instance, monitoring, by the one or more processors, the autoregulation status of the patient based on the relationship between the oxygen saturation gradient and the blood pressure gradient without determining the COx value.

18. The method of claim 17, further comprising:

determining, by the one or more processors, an absolute value of the oxygen saturation gradient; and determining, by the one or more processors, that an autoregulation system of the patient is impaired in response to a determination that the absolute value of the oxygen saturation gradient exceeds an oxygen saturation gradient threshold, that the absolute value of the blood pressure gradient exceeds a blood pressure gradient threshold, and that the oxygen saturation gradient and the blood pressure gradient trend together over the period of time.

19. The method of claim 17, further comprising:

setting, by the one or more processors, a current instantaneous autoregulation status for a first blood pressure monitored over the period of time based on the determined autoregulation status;

modifying, by the one or more processors, the current instantaneous autoregulation status based on a prior instantaneous autoregulation status to generate an updated autoregulation status for the first blood pressure; and presenting, by the one or more processors, an indication of the updated autoregulation status via a display.

20. The method of claim 17, further comprising:

determining, by the one or more processors, an absolute value of the oxygen saturation gradient; and determining, by the one or more processors, that an autoregulation system of the patient is intact if the absolute value of the oxygen saturation gradient exceeds an oxygen saturation gradient threshold over the period of time and if the absolute value of the blood pressure gradient does not exceed a blood pressure gradient threshold over the period of time.

* * * * *